(12) United States Patent
Kronner et al.

(10) Patent No.: US 8,485,484 B2
(45) Date of Patent: Jul. 16, 2013

(54) INSTRUMENT ASSEMBLY SUPPORT APPARATUS

(76) Inventors: Richard F Kronner, Roseburg, OR (US); David D Kronner, Roseburg, OR (US)

(*) Notice: Subject to any disclaimer, the term of this patent is extended or adjusted under 35 U.S.C. 154(b) by 244 days.

(21) Appl. No.: 13/098,284

(22) Filed: Apr. 29, 2011

(65) Prior Publication Data

US 2011/0266407 A1 Nov. 3, 2011

Related U.S. Application Data

(60) Provisional application No. 61/343,521, filed on Apr. 30, 2010.

(51) Int. Cl.
*E04G 3/00* (2006.01)

(52) U.S. Cl.
USPC ............. 248/279.1; 248/287.1; 600/102; 600/229

(58) Field of Classification Search
USPC ............ 248/278.1, 279.1, 231.51, 276.1, 248/287.1, 288.51; 600/102, 228, 229; 269/74; 403/83
See application file for complete search history.

(56) References Cited

U.S. PATENT DOCUMENTS

| | | |
|---|---|---|
| 114,243 A | 4/1871 | Wood et al. |
| 373,362 A | 11/1887 | Hamilton |
| 837,642 A | 12/1906 | Powell |
| 1,084,427 A | 1/1914 | Hanks |
| 1,403,863 A | 1/1922 | Peat |
| 3,810,462 A | 5/1974 | Szpur |
| 4,018,412 A | 4/1977 | Kees, Jr. et al. |
| 4,142,632 A | 3/1979 | Sandel |
| 4,170,336 A | 10/1979 | Malis |
| D263,076 S | 2/1982 | Sandel |
| D263,745 S | 4/1982 | Sandel |
| 4,355,631 A | 10/1982 | LeVahn |
| 4,417,710 A | 11/1983 | Adair |
| D275,229 S | 8/1984 | Sanderson et al. |
| 4,573,452 A | 3/1986 | Greenberg |
| 4,596,329 A | 6/1986 | Eldridge, Jr. |
| 4,597,493 A | 7/1986 | Bruso |
| 4,617,916 A | 10/1986 | LeVahn et al. |
| 4,796,846 A | 1/1989 | Meier et al. |
| 4,863,133 A | 9/1989 | Bonnell |
| 4,867,404 A | 9/1989 | Harrington et al. |
| D306,481 S | 3/1990 | Lang |
| 5,082,111 A | 1/1992 | Corbitt, Jr. et al. |
| 5,104,103 A | 4/1992 | Auchinleck et al. |
| 5,186,174 A | 2/1993 | Schlondorff et al. |
| 5,205,522 A | 4/1993 | Nakamura |

(Continued)

OTHER PUBLICATIONS

US Patent and Trademark Office, Office Action for U.S. Appl. No. 12/582,605, May 24, 2012, 6 pages.

(Continued)

*Primary Examiner* — Bradley Duckworth
(74) *Attorney, Agent, or Firm* — Kolisch Hartwell, PC

(57) ABSTRACT

An instrument assembly support apparatus is disclosed. In some embodiments, the instrument assembly support apparatus may be for supporting an instrument assembly. The instrument assembly may include an instrument support arm. In some embodiments, the instrument assembly support apparatus may include a base fixedly mountable onto the external frame, a pivot assembly mounted for pivoting relative to the base, an arm assembly extending along a longitudinal axis, and a support assembly configured to support the instrument assembly on the arm assembly.

9 Claims, 50 Drawing Sheets

U.S. PATENT DOCUMENTS

| | | | |
|---|---|---|---|
| 5,224,680 | A | 7/1993 | Greenstein et al. |
| 5,284,130 | A | 2/1994 | Ratliff |
| 5,380,338 | A | 1/1995 | Christian |
| 5,383,637 | A | 1/1995 | Biber |
| D358,642 | S | 5/1995 | Michelson |
| 5,441,042 | A | 8/1995 | Putman |
| 5,494,034 | A | 2/1996 | Schlondorff et al. |
| 5,513,827 | A | 5/1996 | Michelson |
| 5,558,622 | A | 9/1996 | Greenberg |
| 5,562,300 | A | 10/1996 | Nelson |
| 5,571,072 | A | 11/1996 | Kronner |
| 5,649,946 | A | 7/1997 | Bramlet |
| 5,662,300 | A | 9/1997 | Michelson |
| 5,681,325 | A | 10/1997 | Hasson |
| 5,785,643 | A | 7/1998 | Lynn |
| 5,810,712 | A | 9/1998 | Dunn |
| 5,810,864 | A | 9/1998 | Schaller |
| 5,824,007 | A | 10/1998 | Faraz et al. |
| 5,836,453 | A | 11/1998 | Herrera |
| 5,876,325 | A | 3/1999 | Mizuno et al. |
| 5,907,664 | A | 5/1999 | Wang et al. |
| 5,918,844 | A | 7/1999 | Ognier |
| 5,957,423 | A | 9/1999 | Kronner |
| 6,080,181 | A | 6/2000 | Jensen et al. |
| 6,179,262 | B1 * | 1/2001 | Ellard et al. ............... 248/276.1 |
| 6,200,263 | B1 | 3/2001 | Person |
| 6,210,325 | B1 * | 4/2001 | Bartie et al. .................. 600/229 |
| 6,213,671 | B1 | 4/2001 | Chang |
| 6,413,264 | B1 | 7/2002 | Jensen et al. |
| 6,461,372 | B1 | 10/2002 | Jensen et al. |
| 6,491,273 | B2 * | 12/2002 | King et al. ................. 248/276.1 |
| 6,540,739 | B2 | 4/2003 | Lechot |
| 6,575,298 | B1 | 6/2003 | McArthur et al. |
| 6,610,009 | B2 | 8/2003 | Person |
| 6,613,039 | B1 | 9/2003 | Namba |
| 6,622,980 | B2 | 9/2003 | Boucher et al. |
| 6,632,170 | B1 | 10/2003 | Bohanan et al. |
| 6,663,055 | B2 * | 12/2003 | Boucher et al. ............... 248/118 |
| 6,716,163 | B2 | 4/2004 | Muhanna et al. |
| 6,966,876 | B2 | 11/2005 | Irion et al. |
| 6,969,192 | B1 | 11/2005 | Hollowell |
| 6,971,617 | B2 | 12/2005 | Nguyen |
| 7,179,225 | B2 | 2/2007 | Shluzas et al. |
| 7,670,281 | B2 | 3/2010 | Kronner |
| 2006/0079864 | A1 | 4/2006 | Kronner |
| 2010/0108841 | A1 | 5/2010 | Kronner et al. |
| 2010/0114117 | A1 | 5/2010 | Kronner |

OTHER PUBLICATIONS

US Patent and Trademark Office, Office Action for U.S. Appl. No. 12/684,296 dated Dec. 11, 2012, 22 pages.

Stoney, Ronald J., M.D., "How to Achieve Optimum Exposure of the Upper Abdominal Aorta and Its Branches", Minnesota Scientific Inc., Dec. 1986, pp. 1-4.

Cuschieri, Alfred, M.D., "Minimum Access Surgery and the Future of Interventional Laparoscopy", The American Journal of Surgery, Mar. 1991, vol. 161, pp. 404-407.

Omni-Tract Surgical: a Division of Minnesota Scientific, Inc., Literature on the Omni-Tract Corral Retractor, Pittman IMA Retractor System, Omni-LapoTract Support Systems, and Omni-Tract Accessories, 1991 and 1993, 8 pages, Omni-Tract Surgical, St. Paul, Minnesota.

Omni-Tract Surgical: a Divison of Minnesota Scientific, Inc., Catalog featuring surgical components, retractors, blades, and accessories, 1991, 8 pages, Omni-Tract Surgical, St. Paul, Minnesota.

Nathanson et al., "Laparoscopic Cholecystectomy: the Dundee technique", Br. J. Surg., Feb. 1991,vol. 78, No. 2, pp. 155-159, Butterworth-Heinemann Ltd.

Omni-Tract Surgical: a Division of Minnesota Scientific, Inc., "Stoney Mini Vascular Retractor System—VM100", 1991, 4 pages, Omni-Tract Surgical, St. Paul, Minnesota.

Berci et al., "New Ideas and Improved Instrumentation for Laparoscopic Cholecystectomy", Surgical Endoscopy, 1991, vol. 5, pp. 1 and 3, Springer-Verlag, Los Angeles, California.

Leonard Medical, Inc., Literature on the Leonard Arm, Leonard Arm Jr., Laparoscope Holder and Instrument Holder, Oct. 20, 1993, 11 pages, Leonard Medical, Inc., Huntingdon Valley, Pennsylvania.

NASA Tech Briefs, "Robotics for Safer Surgery", Jan. 1994, vol. 18, No. 1, pp. 16-18.

Allen Medical Systems, "Leonard Arm Scope & Retractor Holders", 1996, 7 pages.

Computer Motion, Inc., "AESOP: Automated Endoscope System for Optimum Positioning", Fall 1997, 5 pages, Computer Motion, Inc., Goleta, California.

World of Medicine Lemke GmbH, "510(K) Summary SightFix", stamped Mar. 18, 2003, 2 pages.

Jaspers et al., Abstract of "Camera and Instrument Holders and Their Clinical Value in Minimally Invasive Surgery", Surgical Laparoscopy Endoscopy & Percutaneous Techniques, Jun. 2004, vol. 14(3), 1 page, Lippincott Williams & Wilkins.

Richard M. Kronner, M.D., "Letter to Peter Sabido of Kolisch Hartwell", 2 pages.

Thompson Surgical Instruments, Inc., "Thompson Scope Holder", downloaded from http://www.thompsonsurgical.com on Feb. 17, 2006, 1 page.

Thompson Surgical Instruments, Inc, "Flexbar/Thompson Scope Holder", downloaded from http://www.thompsonsurgical.com on Feb. 17, 2006, 1 page.

UCI Medical Center, "Smooth Operator: The Surgical Robot", downloaded from www.ucihealth.com on Feb. 21, 2006, 2 pages, UCI Medical Center, University of California Irvine.

Omni-Tract Surgical: a Division of Minnesota Scientific, Inc., "Omni-Lapo Tract Scope and Instrument Holder", 2006, 2 pages, Omni-Tract Surgical, St. Paul, Minnesota.

Computer Motion, Inc., "Enhancing Performance Through Robotics" and "Robotic Enhancement Technology", no date, 2 pages, Computer Motion, Inc., Goleta, California.

Computer Motion, Inc., "AESOP: Automated Endoscope System for Optimum Positioning", no date, 4 pages, Computer Motions, Inc., Goleta, California.

Omni-Tract Surgical: a Division of Minnesota Scientific, Inc., "FastSystem Stoney Peripheral Vascular Retractor System—VF100", no date, 2 pages, Omni-Tract Surgical, St. Paul, Minnesota.

Unknown, The Iron Intern Robotic Retractor—Your Most Dependable Assistant, no date, 2 pages.

Elmed, Inc., "Elmed Endoscopic Fixation Device", 4 pages, Elmed, Inc., Addison, Illinois.

Armstrong Healthcare Limited, "EndoAssist: The Camera Manipulator for Laparoscopic Surgery", no date; 1 page.

Mediaflex, Advertisement titled "Surgical Devices Since 1969", no date, 1 page.

Lerner et al, "A Passive Positioning and Supporting Device for Surgical Robots and Instrumentation", no date, pp. 1-11, John Hopkins University, Department of Mechanical Engineering, Baltimore, Maryland.

US Patent and Trademark Office, Office Action for U.S. Appl. No. 12/582,605, Feb. 2, 2012, 9 pages.

* cited by examiner

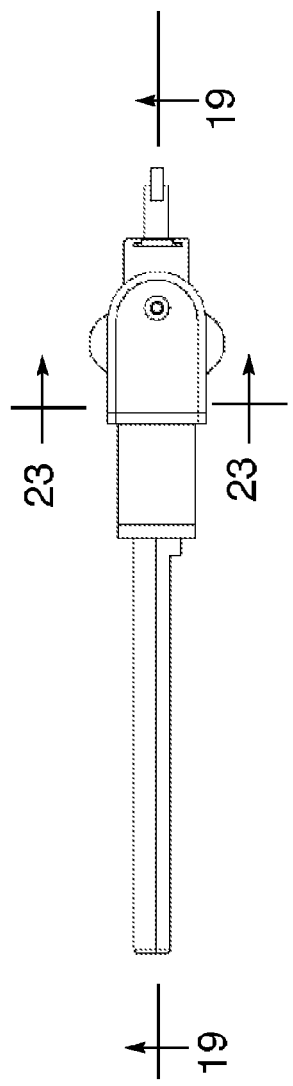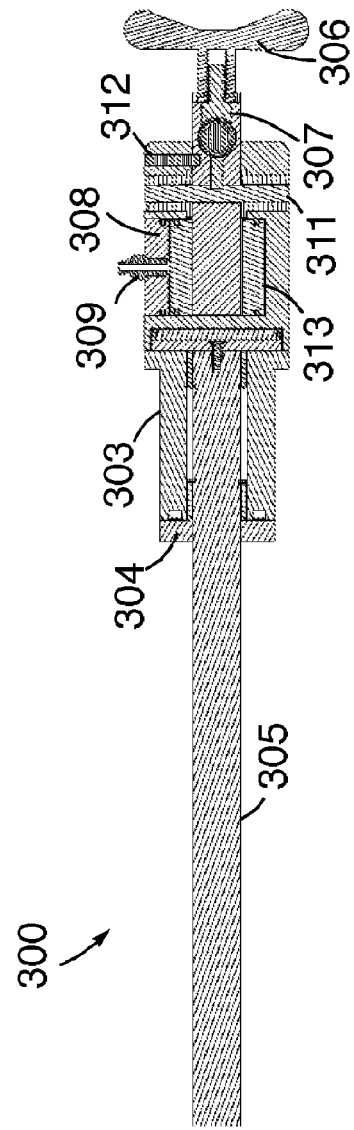

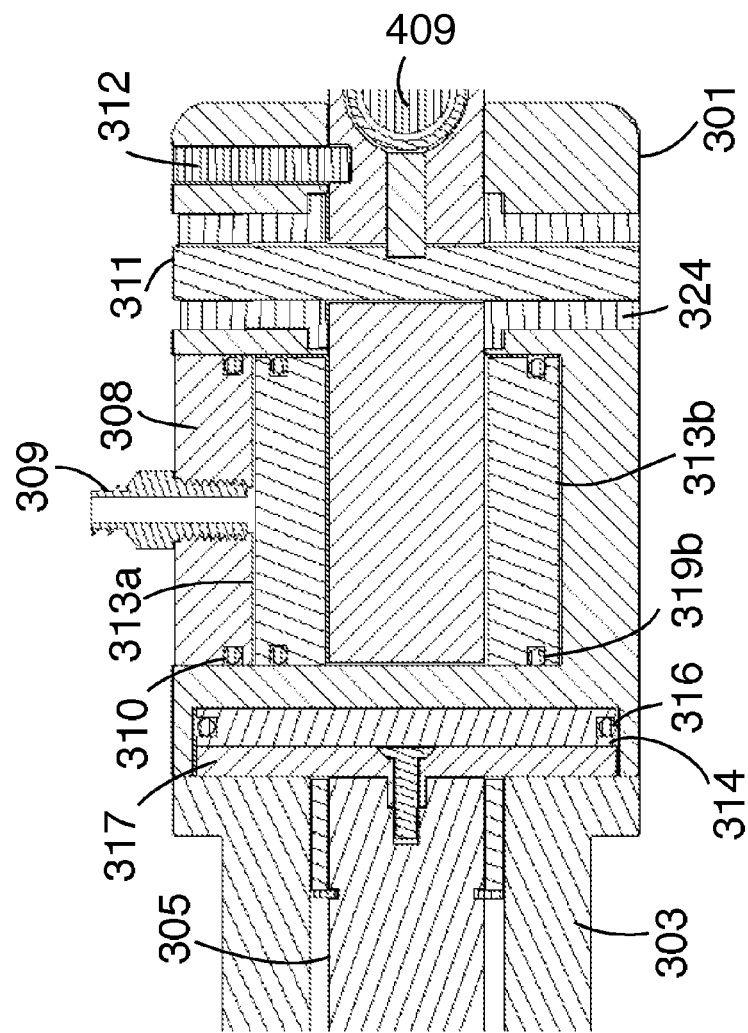

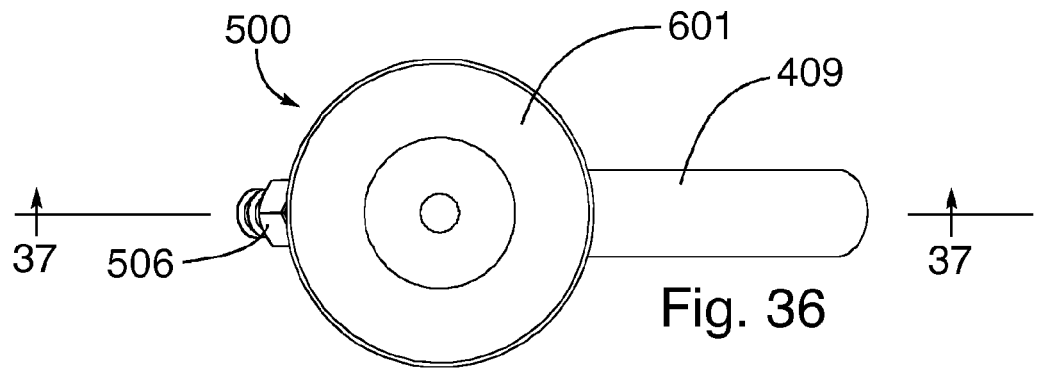
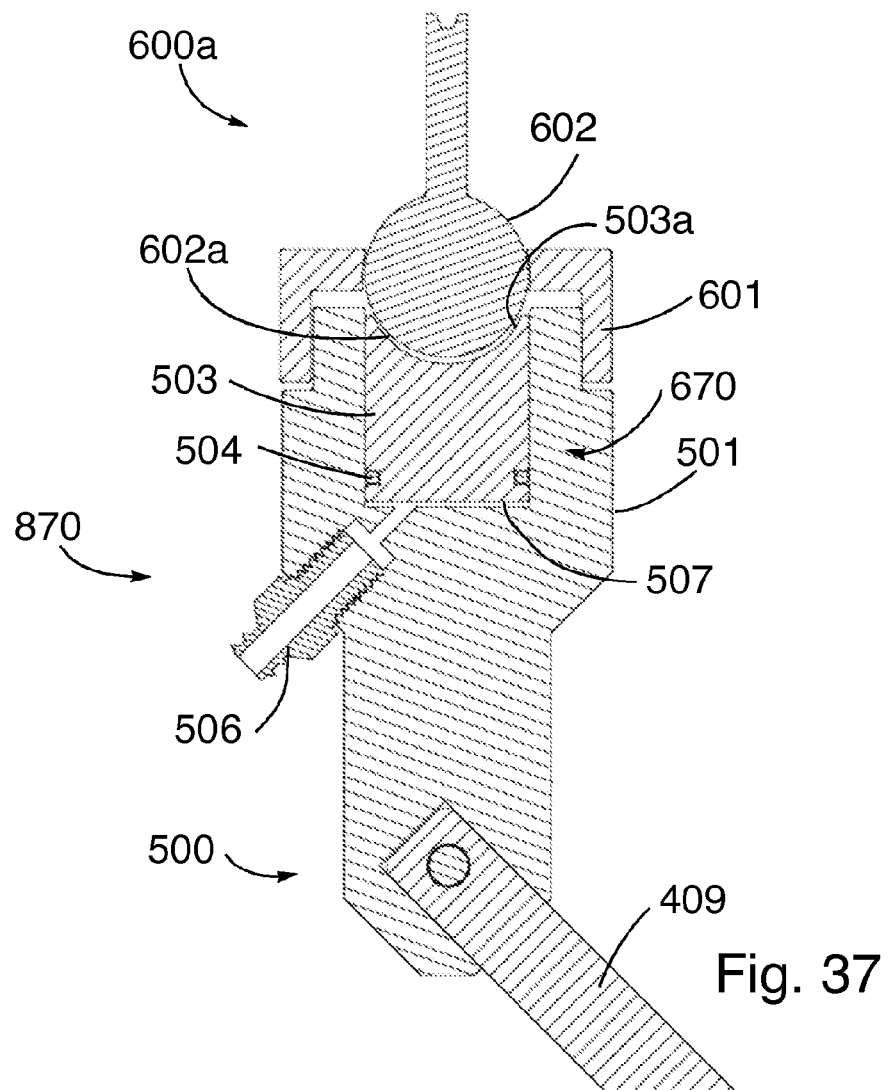

INSTRUMENT ASSEMBLY SUPPORT APPARATUS

CROSS-REFERENCE TO RELATED APPLICATIONS

This application claims priority under 35 U.S.C. §119(e) to U.S. Provisional Patent Application Ser. No. 61/343,521 entitled "Surgical Instrument Holder," filed Apr. 30, 2010, the complete disclosure of which is hereby incorporated by reference for all purposes.

BACKGROUND OF THE DISCLOSURE

Laparoscopic, vaginal, and/or other perineal surgery may involve the use of one or more instrument assemblies, such as uterine manipulators, retractors, viewing scopes, etc. Throughout the procedure the surgeon, assistant surgeon, or a scrub nurse must hold the instrument assembly and direct it at the target of the surgery, which may entail constantly repositioning the instrument assembly, such as a scope to obtain the best view. This process ties up one hand of the surgeon or assistant surgeon, if either holds the instrument assembly. The scrub nurses also have other tasks to perform so holding the instrument assembly interferes with performing these tasks. Additionally, the surgeon typically finds it difficult to direct others to position the instrument assembly. As a result, the instrument assembly is often misdirected when not held by the surgeon.

SUMMARY OF THE DISCLOSURE

Some embodiments of an instrument assembly support apparatus for supporting an instrument assembly relative to a patient positioned adjacent to an external frame. In some embodiments, the instrument assembly support apparatus may include a base fixedly mountable onto the external frame, and a pivot assembly mounted relative to the base and including a housing, a first pivot structure pivotably mounted to the housing and fixedly mounted to the base, and a second pivot structure pivotably mounted to the housing. The housing may be configured to pivot relative to the first pivot structure and the external frame about a first pivot axis, and the second pivot structure may be configured to pivot relative to the housing about a second pivot axis. The housing may include two opposed and spaced side portions and a base portion connecting the two side portions to define a gap between the two side portions. The second pivot structure may be disposed within the gap with at least one surface of the second pivot structure extending through the gap over a range of pivot positions about the second pivot axis.

The instrument assembly support apparatus may additionally include an arm assembly extending along a longitudinal axis and having a first portion mounted to the at least one surface of the second pivot structure for pivoting relative to the housing, and a second portion extending distally of the first portion. The instrument assembly support apparatus may further include a support assembly mounted to the second portion and configured to support the instrument assembly on the arm assembly, and a first lock assembly mounted to the housing and configured to be remotely actuated to lock the first pivot structure relative to the housing. The first lock assembly may include first and second opposing planar faces intersected by the first pivot axis, a first stop, and a biasing mechanism. The first face may be mounted to the first pivot structure, and the second face may be disposed to move normal to the first face. The first stop may be configured to prevent pivoting of the second face about the first pivot axis, and the biasing mechanism may be configured to selectively bias the second face toward the first face.

In some embodiments, the instrument assembly support apparatus may include a base fixedly mountable onto the external frame, and a pivot assembly mounted relative to the base and having a pivot structure. The pivot structure may be configured to pivot relative to the base about a pivot axis. The instrument assembly support apparatus may additionally include n arm assembly extending along a longitudinal axis, a first portion supported by the housing and mounted to the pivot structure for pivoting relative to the base, and a second portion supported by the housing and extending distally of the first portion.

The instrument assembly support apparatus may further include a support assembly mounted to the second portion and configured to support the instrument assembly on the arm assembly, and a lock assembly configured to be remotely actuated to lock one of the first and second portions relative to the other of the first and second portions. The lock assembly may include first and second opposing pressure pads and a biasing mechanism, each of the first and second pressure pads including a channel portion, with the channel portions facing each other to form a channel through which the one of the first and second portions extends between the first and second pressure pads. The biasing mechanism may be configured to selectively bias the first and second pressure pads toward the one of the first and second portions.

Some embodiments of an instrument assembly support apparatus for supporting an instrument assembly relative to a patient positioned adjacent to an external frame. The instrument assembly may include an instrument support arm and a joint assembly having a first connector and a first joint element received in the first connector. The first joint element may be configured to allow for movement of the instrument support arm along plural axes relative to the connector. In some embodiments, the instrument assembly support apparatus may include a base fixedly mountable onto the external frame, and a pivot assembly mounted relative to the base and having a pivot structure configured to provide pivoting relative to the base about a pivot axis.

The instrument assembly support apparatus may additionally include an arm assembly extending along a longitudinal axis and having a first portion mounted to the pivot structure for pivoting relative to the base, and a second portion extending distally of the first portion, and a support assembly mounted to the second portion and configured to support the instrument assembly on the arm assembly. The support assembly may include a housing and a second connector that is configured to mate with the first connector. The instrument assembly support apparatus further including a lock assembly mounted to the housing and configured to be remotely actuated to lock the first joint element relative to the first connector. The lock assembly may include a pressure pad and a biasing mechanism. The biasing mechanism may be configured to selectively bias the pressure pad toward the first joint element.

BRIEF DESCRIPTION OF THE DRAWINGS

FIG. 18 is a top view of the pivot assembly of FIG. 13.

FIG. 19 is a cross-sectional view of the pivot assembly of FIG. 13 taken along lines 19-19 in FIG. 18.

FIG. 20 is a partial view of the pivot assembly of FIG. 19, showing a first portion of the pivot assembly of the instrument assembly support apparatus of FIG. 2.

FIG. 36 is a top view of a support assembly of FIG. 35, showing a partial view of an instrument assembly attached to the support assembly.

FIG. 37 is a cross-sectional view of the support assembly of FIG. 35 taken along lines 37-37 in FIG. 36, showing a partial view of an instrument assembly attached to the support assembly.

DETAILED DESCRIPTION OF THE DISCLOSURE

Figure 1:
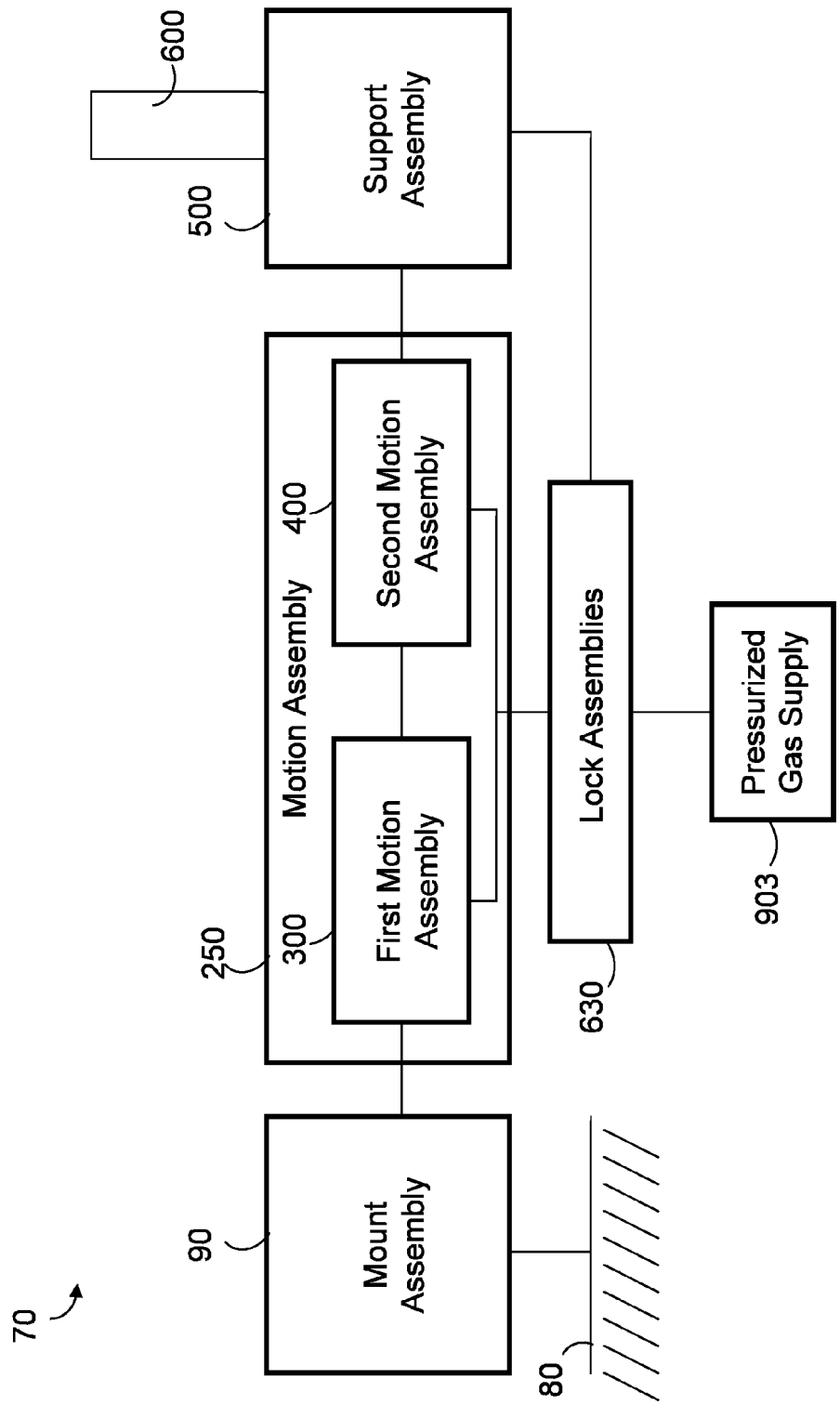
FIG. 1 is a schematic view of an instrument assembly support apparatus.
Figure 2:
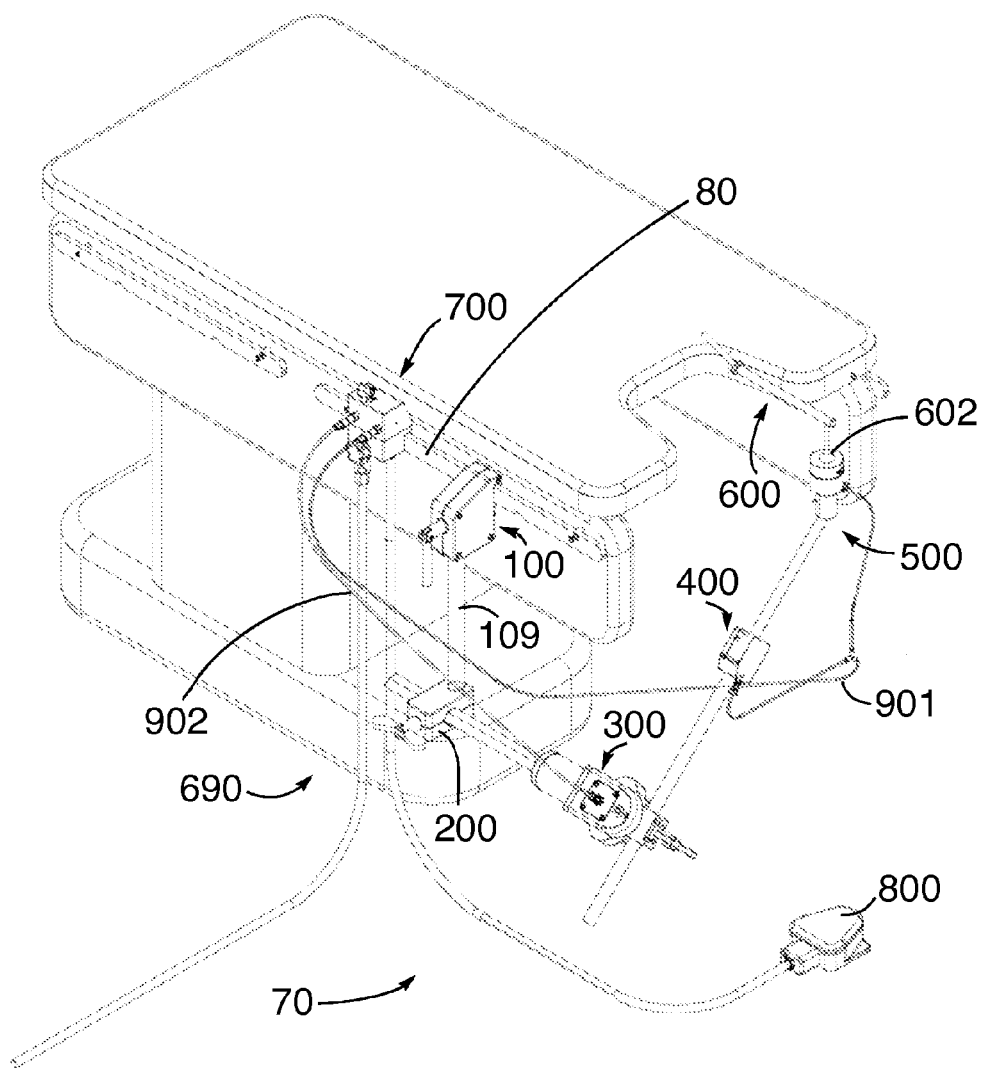
FIG. 2 is an isometric view of an illustrative example of the instrument assembly support apparatus of FIG. 1 attached to an operating table.

FIGS. 1-2 depict some embodiments of an instrument assembly support apparatus 70. The instrument assembly support apparatus may support an instrument assembly 600, such as a uterine manipulator and/or retractor (and/or a holder for such instrument), relative to an operating table having an external frame 80 (such as a rail). A patient may be positioned adjacent to the external frame. Although instrument assembly support apparatus 70 may be shown in one or more figures of this disclosure to be supporting a particular instrument and/or instrument holder, the instrument assembly support apparatus may additionally, or alternatively, be configured to support one or more other instruments, and/or one or more other instrument holders, including equipment of any appropriate form, as well.

Figure 3:
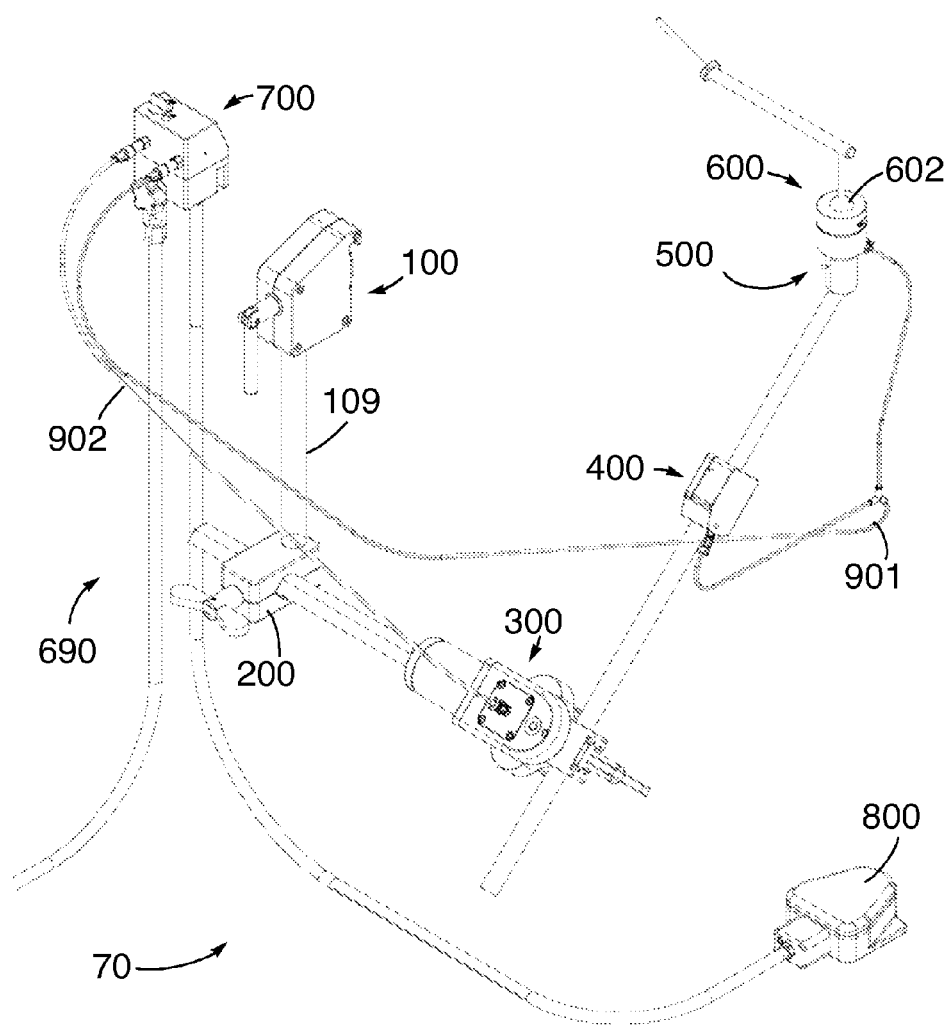
FIG. 3 is an isometric view of the instrument assembly support apparatus of FIG. 2.
Figure 4:
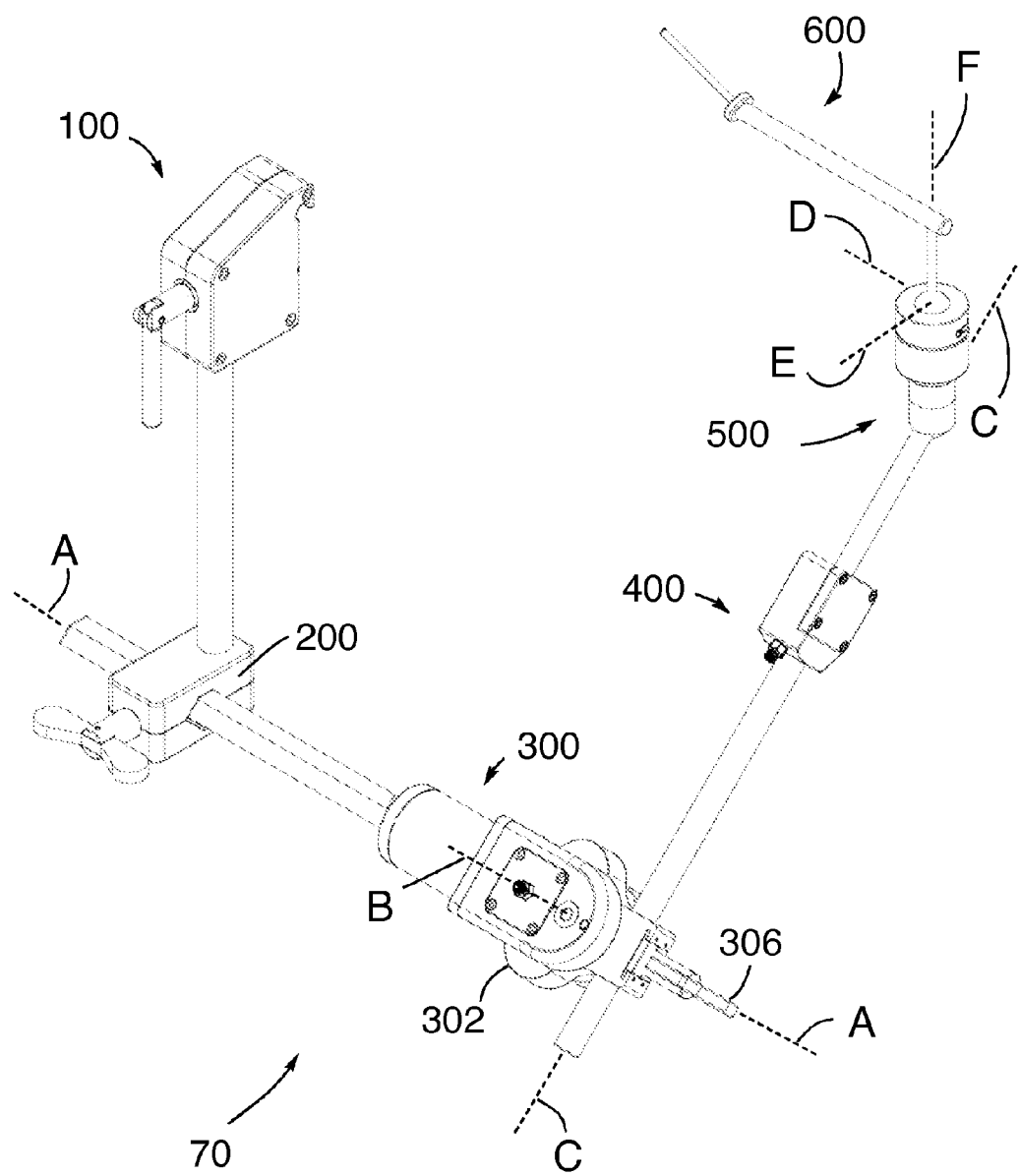
FIG. 4 is an isometric view of the instrument assembly support apparatus of FIG. 2 shown without a gas supply assembly and a pedal assembly, and showing the various axes that a user may move an instrument assembly supported by the instrument assembly support apparatus.
Figure 5:
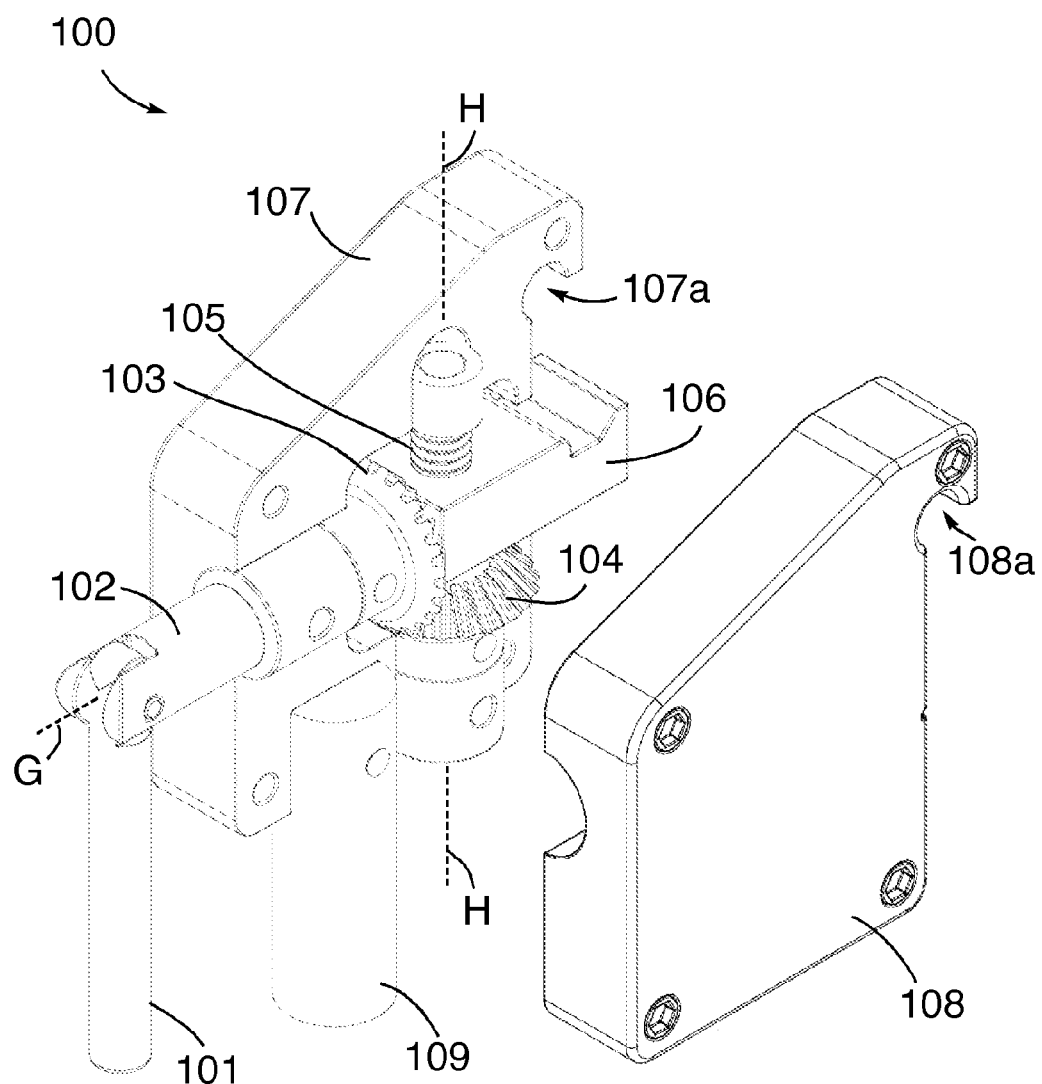
FIG. 5 is an isometric view of a grip assembly of the instrument assembly support apparatus of FIG. 2, showing a housing portion of the grip assembly removed.

The instrument assembly support apparatus may include a base or mount assembly 90, a motion assembly 250, and a support assembly 500, as shown in FIG. 1. Mount assembly 90 may include any suitable structure configured to secure the instrument assembly support apparatus to external frame 80. For example, the mount assembly may include a grip assembly 100 and a connector assembly 200, as shown in FIGS. 3-4.

Figure 6:
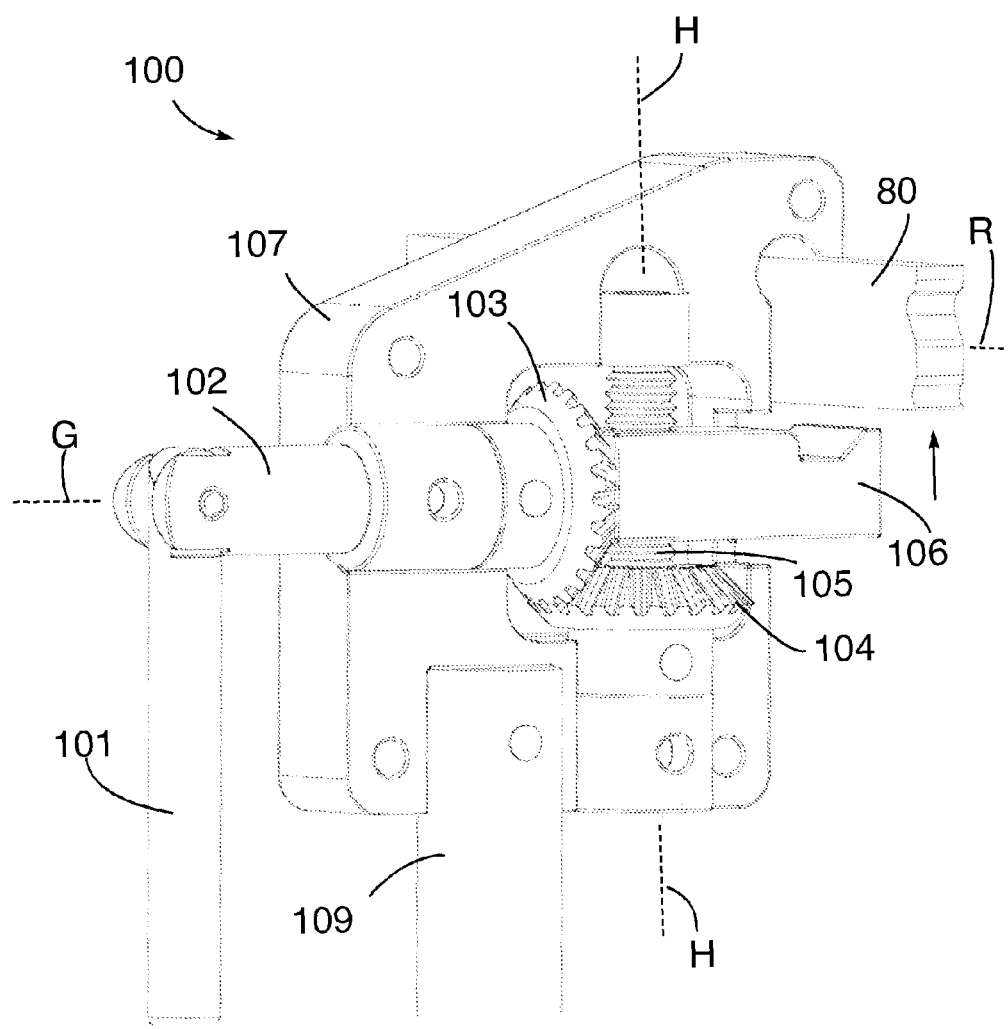
FIG. 6 is an isometric view of the grip assembly of FIG. 5 with a housing portion removed, showing a grip portion of the other housing portion of the grip assembly contacting an external frame.
Figure 7:
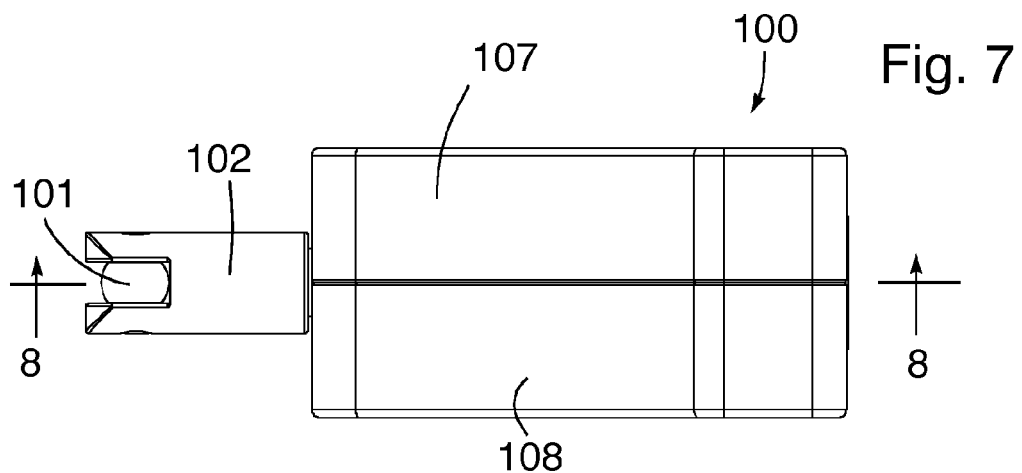
FIG. 7 is a top view of the grip assembly of FIG. 5.
Figure 8:
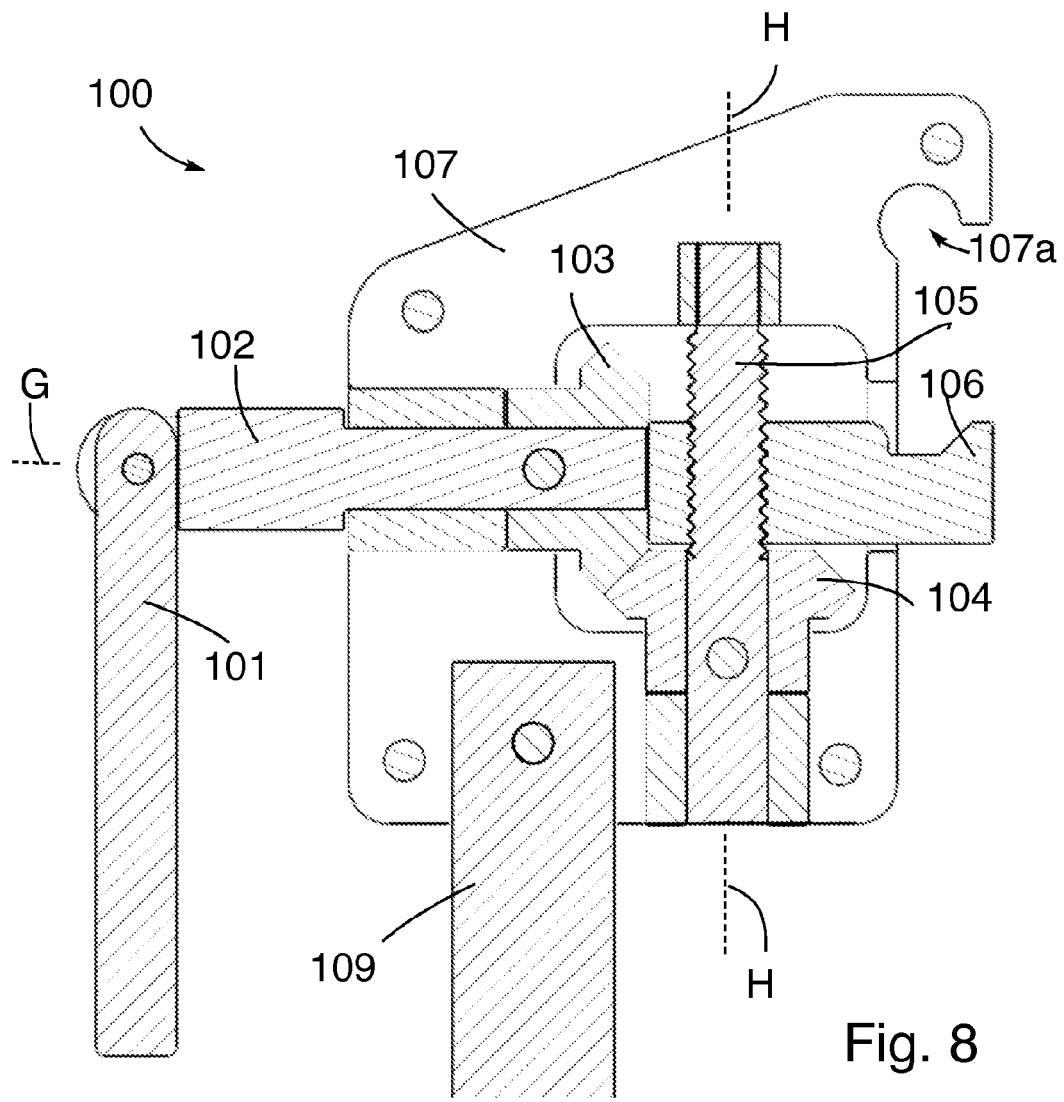
FIG. 8 is a cross-sectional view of grip assembly of FIG. 5 taken along lines 8-8 shown in FIG. 7.
Figure 9:
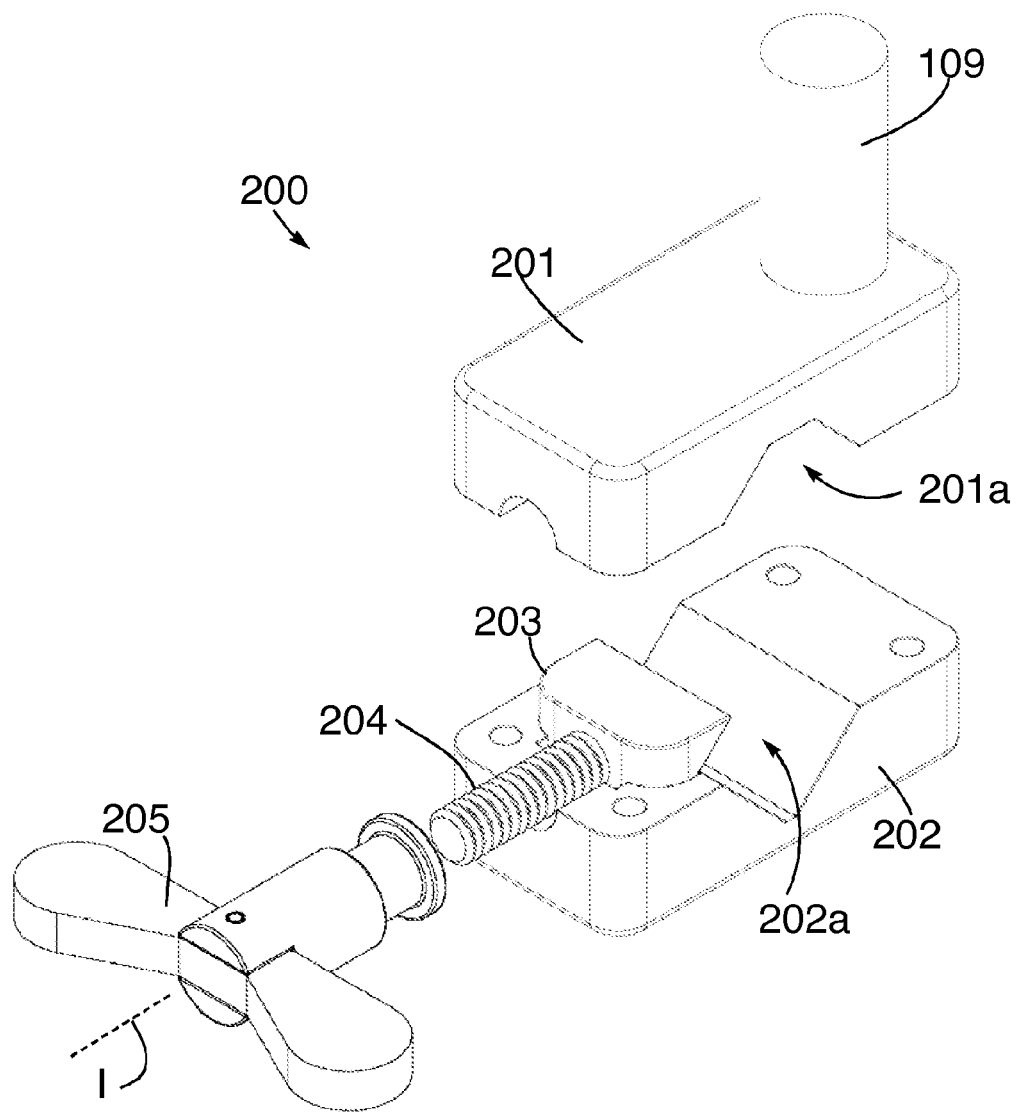
FIG. 9 is an exploded view of a connector assembly of the instrument assembly support apparatus of FIG. 2.
Figure 10:
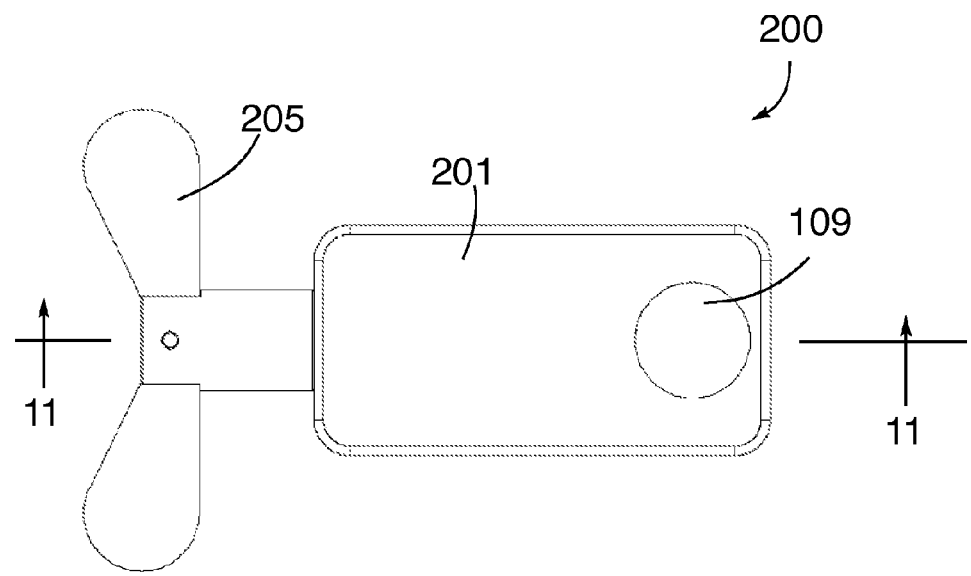
FIG. 10 is a top view of the connector assembly of FIG. 9.
Figure 11:
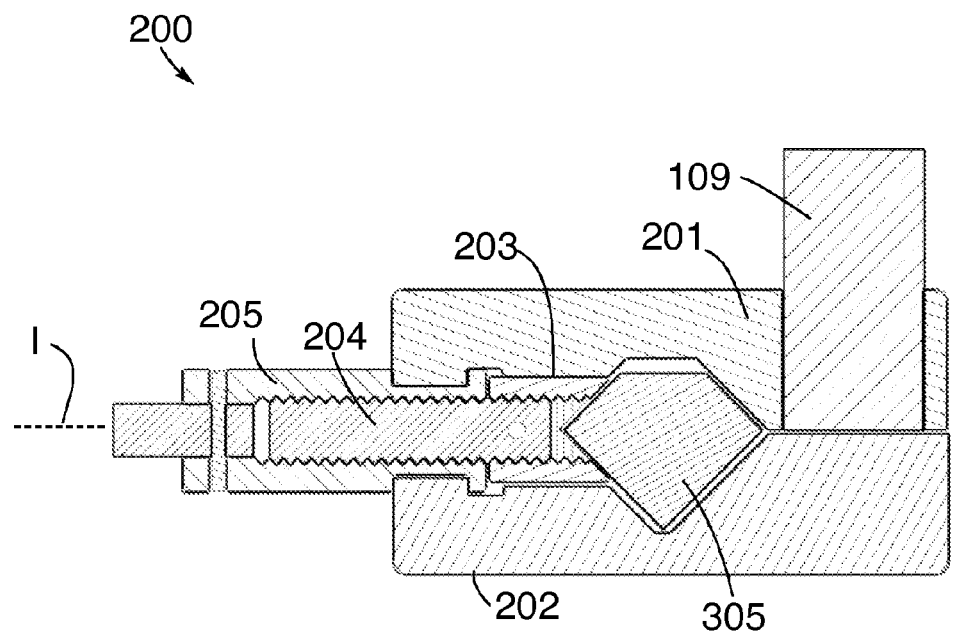
FIG. 11 is a cross-sectional view of the connector assembly of FIG. 9 taken along lines 11-11 shown in FIG. 10, showing the connector assembly attached to a first pivot structure of a pivot assembly of the instrument assembly support apparatus of FIG. 2.
Figure 12:
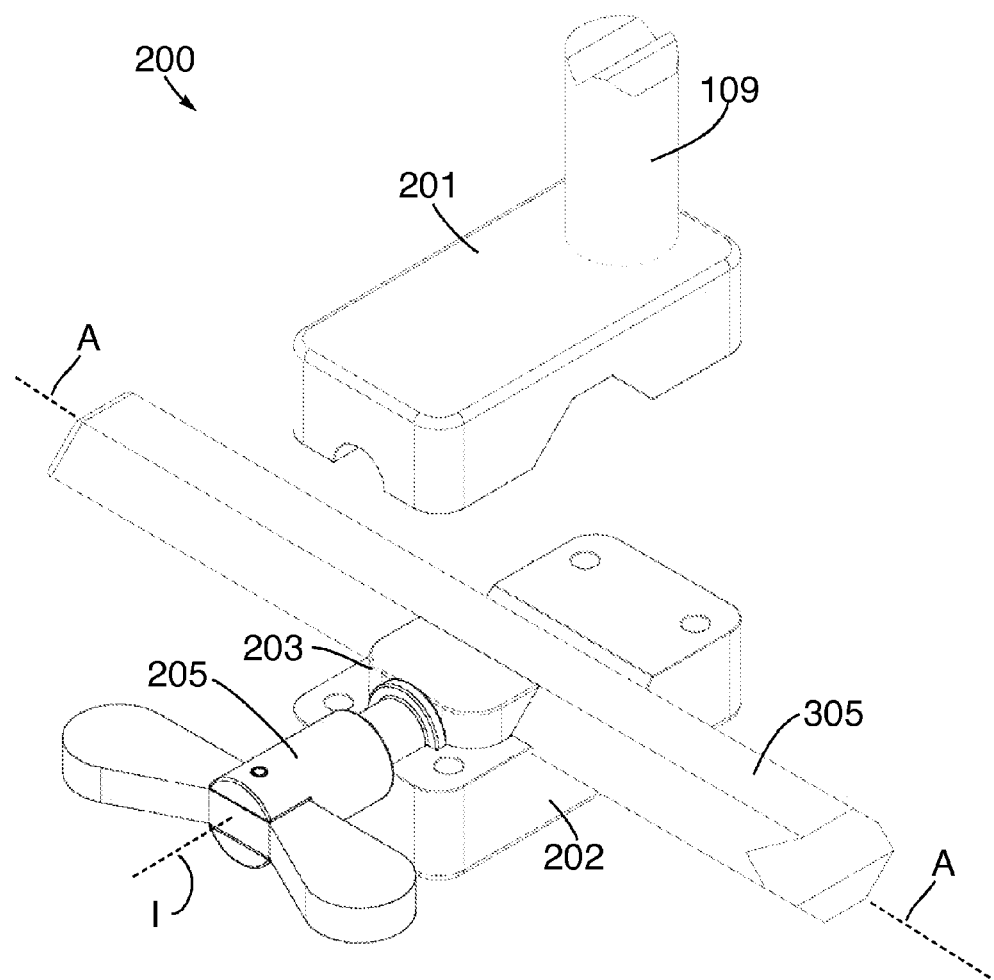
FIG. 12 is an exploded view of the connector assembly of FIG. 9, showing a first pivot structure of a pivot assembly received in a channel of the connector assembly.

Grip assembly 100 may include any suitable structure configured to be fixedly mountable onto external frame 80 or be securable to the external frame in any other suitable way. For example, the grip assembly may include a handle 101, a first shaft 102, gears 103 and 104, a second shaft 105, a movable grip 106, first and second housing portions 107 and 108, and an elongate support member or rod 109, as shown in FIGS. 5-8. First and second housing portions 107 and 108 may include grip portions 107a and 108a, respectively, that may be configured to rest on external frame 80. Handle 101 may allow a user to selectively move grip 106 against external frame 80, such as a rail that extends along a rail axis R, as shown in FIG. 6. Grip 106 may be configured to selectively grip the external frame with the elongate support member extending away from the grip.

During attachment of grip assembly 100, rotation of handle 101 around an axis G may cause shaft 102 and gear 103 to rotate around axis G. Gear 103 meshes with gear 104, which may cause shaft 105 to rotate around an axis H to drive grip 106 against the external frame.

Connector assembly 200 may include any suitable structure configured to connect grip assembly 100 with one or more other components of the instrument assembly support apparatus. For example, the connector assembly may include first and second housing portions 201 and 202, a sliding grip 203, a shaft 204, and a handle 205, as shown in FIGS. 9-12. Housing portions 201 and 202 may include channel portions 201a and 202a, respectively. Those channel portions may be configured to selectively receive one or more components of motion assembly 250, such as a first pivot structure, in any suitable orientation, such as along an axis A that may be parallel to rail axis R. Additionally, housing portion 201 may be attached to elongate support member 109. During attachment of one or more components of motion assembly 250 to connector assembly 200, rotation of handle 205 around an axis I may cause grip 203 to move via shaft 204 to grip the component(s).

Although mount assembly 90 is shown to include grip assembly 100 and connector assembly 200, the mount assembly may include any suitable structure known in the art. Illustrative examples of suitable structures are disclosed in U.S. Pat. Nos. 5,957,423 and 7,670,281, the complete disclosures of which are hereby incorporated by reference for all purposes. Additionally, although mount assembly 90 is shown to be mounted on a particular external frame, the mount assembly may be configured to be mounted on any suitable type of rigid structure.

Motion assembly 250 may include any suitable structure configured to allow a user to move instrument assembly 600 in any predetermined way(s). For example, motion assembly 250 may include a first motion assembly 300 and a second motion assembly 400, as shown in FIG. 1. Each of the first and second motion assemblies may allow for pivoting, sliding, rotating, and/or otherwise moving of the instrument assembly. For example, first motion assembly 300 may allow for pivoting of the instrument assembly, and may be referred to as "pivot assembly 300." Although first motion assembly 300 may be referred to as "pivot assembly 300," that assembly may also allow for sliding and/or other movements of the instrument assembly.

Additionally, or alternatively, second motion assembly 400 may allow for sliding of the instrument assembly, and may be referred to as "sliding assembly 400." Although second motion assembly 400 may be referred to as "sliding assembly 400," that assembly may also allow for pivoting and/or other movements of the instrument assembly. Additionally, although motion assembly 250 is shown to include particular assemblies configured to allow instrument assembly 600 to be, for example, pivoted and/or slid, the motion assembly may include any suitable assembly or combination of assemblies for any suitable movement(s). For example, motion assembly 600 may include only a pivot assembly, only a sliding assembly, or only a combination pivoting and sliding assembly. Additionally, or alternatively, the motion assembly may include two or more pivot assemblies and/or two or more sliding assemblies.

Pivot assembly 300 may include any suitable structure configured to allow a user to pivot instrument assembly 600 relative to mount assembly 90 about any suitable axis or axes. For example, the pivot assembly may be mounted relative to mount assembly 90 and may include a first pivot structure 300a, a frame or housing 301, and a second pivot structure 302, as shown in FIGS. 13-21. First pivot structure 300a may include any suitable structure configured to allow a user to pivot instrument assembly 600 about a first pivot axis A, as shown in FIG. 4. The first pivot structure may, for example, be pivotably mounted to the frame and fixedly mounted to the base. Additionally, the first pivot structure may allow frame 301 to pivot relative to the first pivot structure and/or the external frame about the first pivot axis. First pivot structure 300a may include a base 304 and a shaft 305, as shown in FIGS. 13-14 and 19-20.

Base 304 may include any suitable structure configured to interact with one or more components of frame 301 to limit pivoting of the frame relative to the first pivot structure within any suitable predetermined number of degrees, such as ninety degrees. For example, base 304 may include at least one stop or pin 318 that may received in a groove of one or more parts of frame 301 (further discussed below). Alternatively, base 304 may include a groove that receives one or more pins of one or more parts of frame 301. Shaft 305 may receive base 304 and may be received in connector assembly 200.

Figure 16:
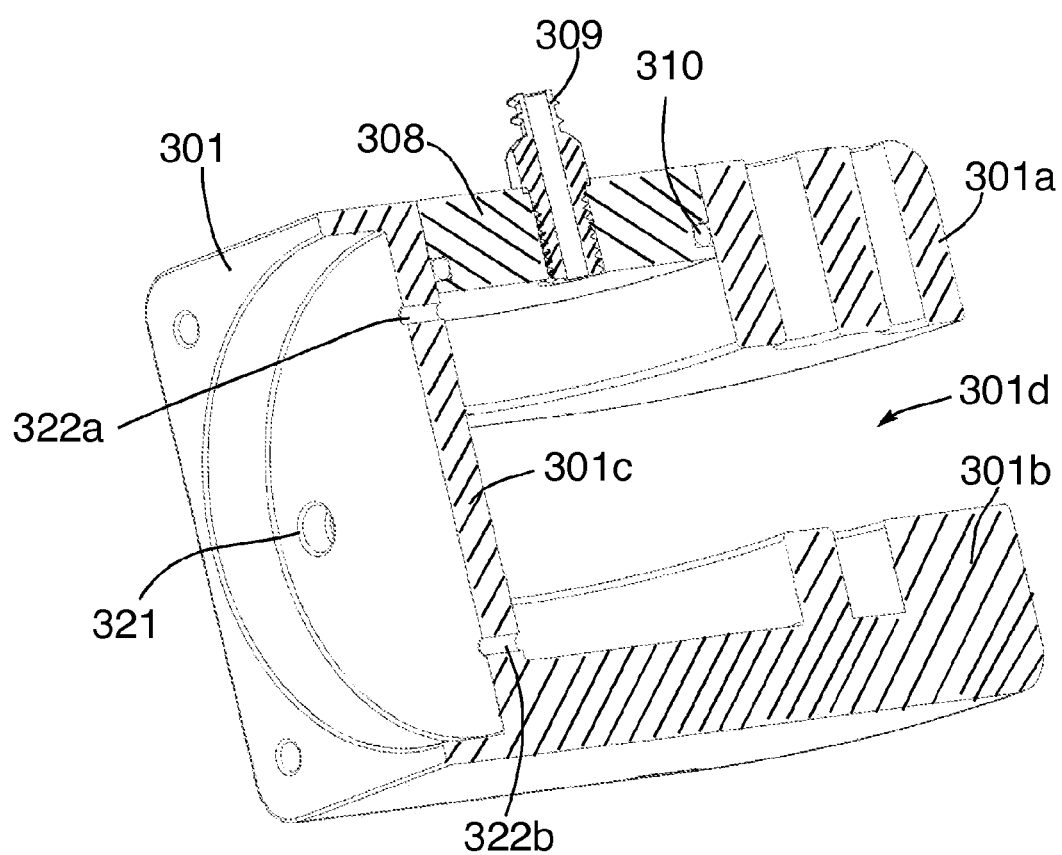
FIG. 16 is an isometric view of the pivot assembly of FIG. 13, showing a housing and a luer of the pivot assembly.

Pivot assembly 300 also may include frame or housing 301, which may include any suitable structure configured to support and/or at least partially contain first pivot structure 300a, second pivot structure 302, and/or any other components of pivot assembly 300. The frame also may at least substantially enclose one or more locking assemblies, as further discussed below. For example, the frame may include two opposed and/or spaced side portions 301a and 301b, and a base portion 301c connecting the two side portions to define a gap 301d between the two side portions, as shown in FIG. 16. The gap may receive second pivot structure 302, as further discussed below.

Figure 13:
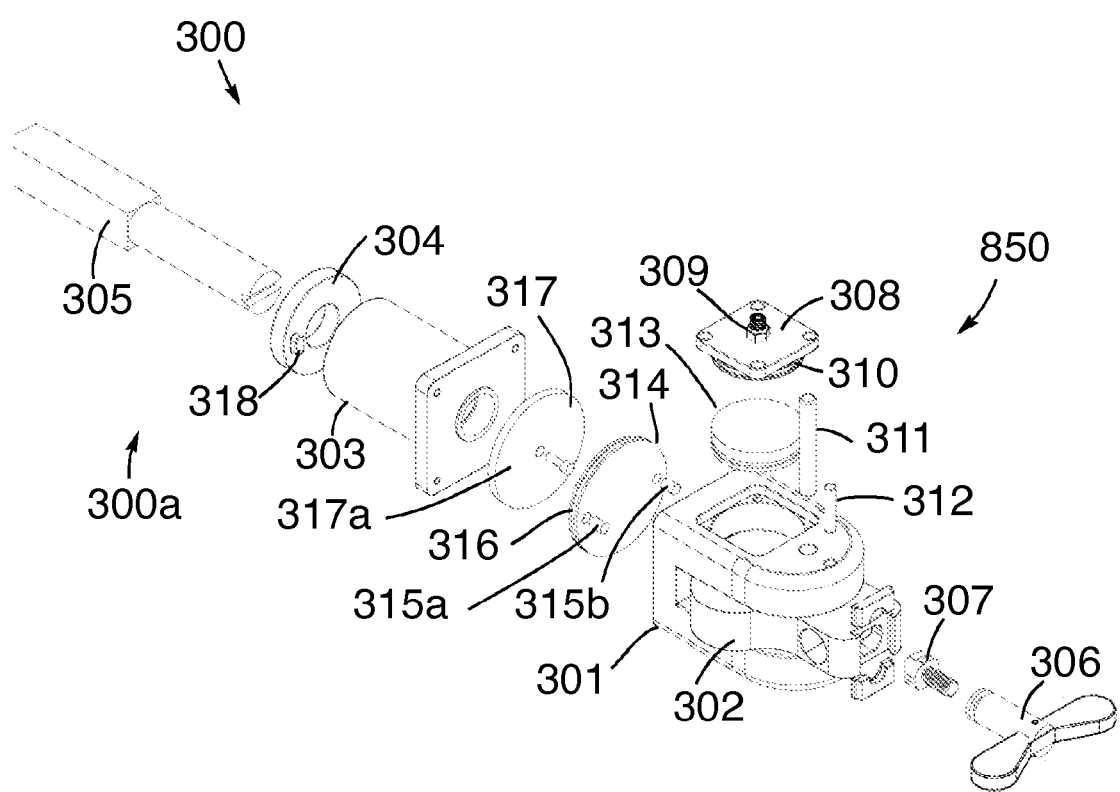
FIG. 13 is an exploded view of a pivot assembly of the instrument assembly support apparatus of FIG. 2.
Figure 14:
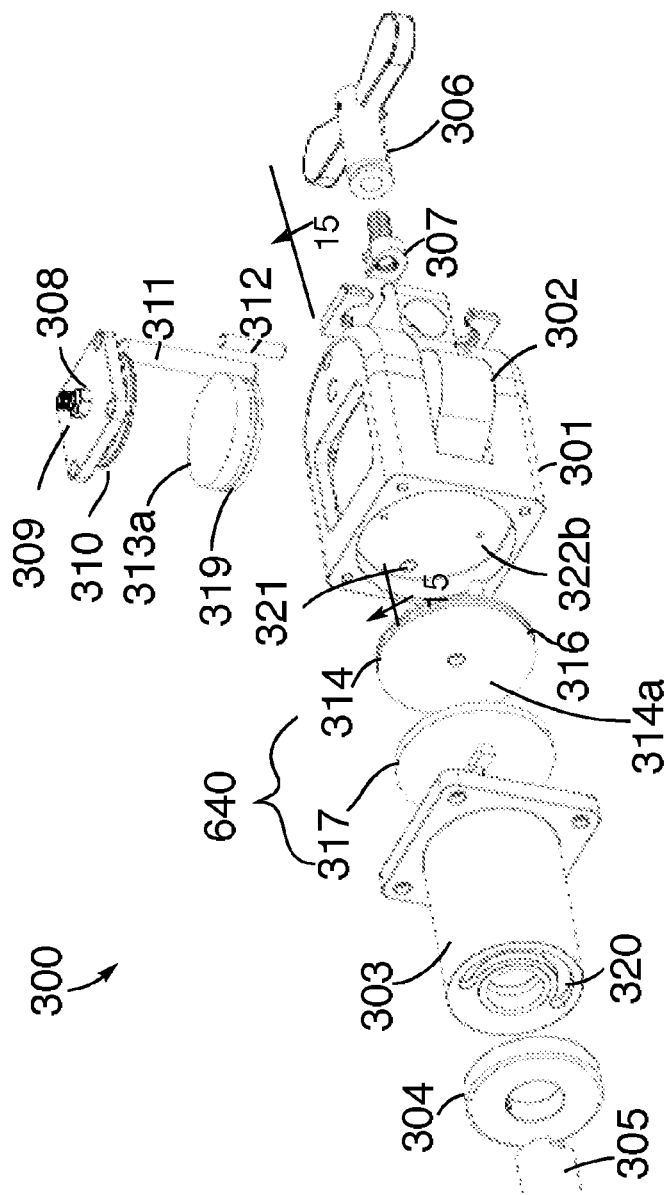
FIG. 14 is another exploded view of the pivot assembly of FIG. 13.
Figure 15:
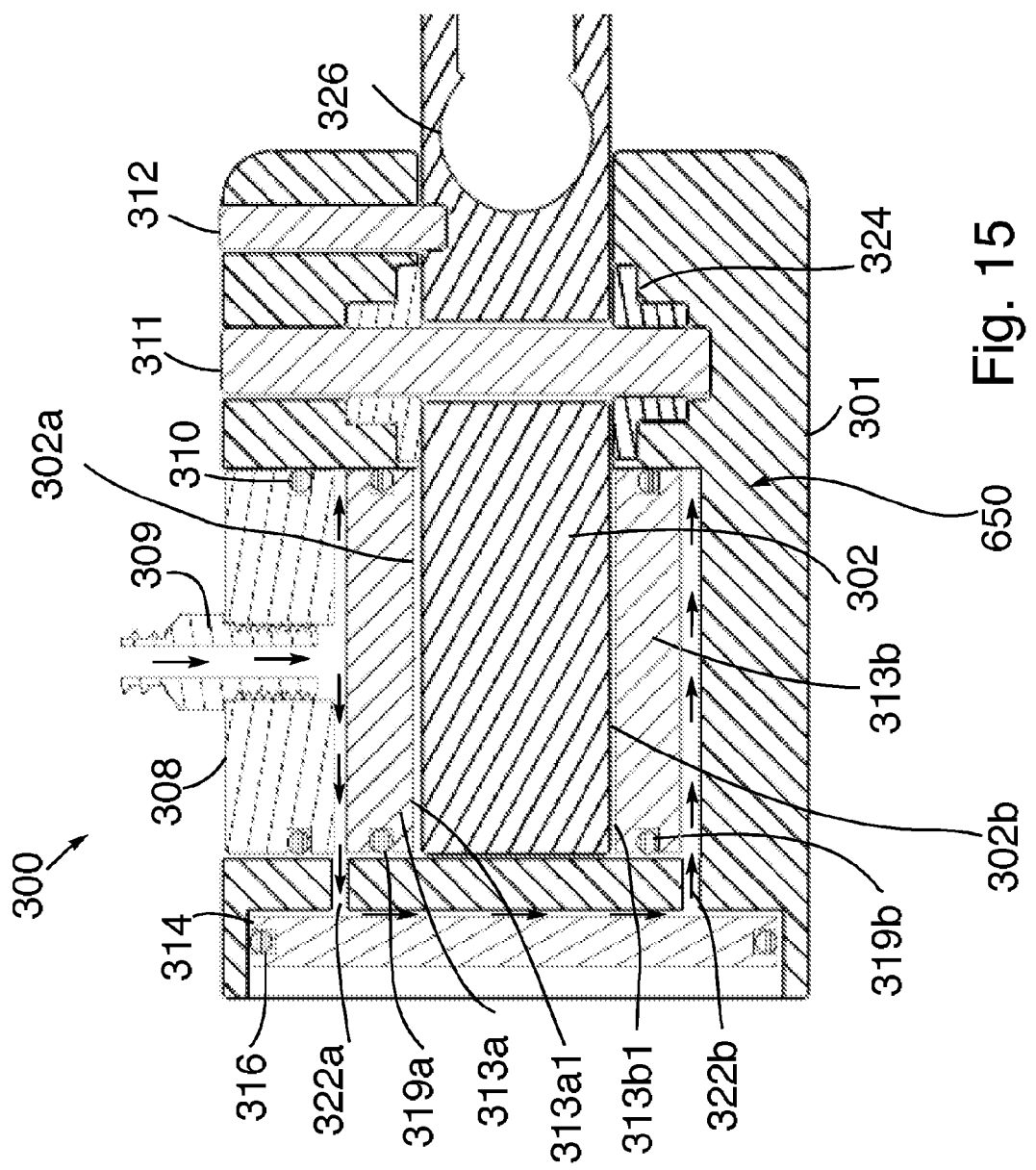
FIG. 15 is a partial cross-sectional view of the pivot assembly of FIG. 13 taken along lines 15-15 in FIG. 14, showing gas flow within the pivot assembly.

Additionally, frame 301 may include a secondary housing 303, a pivot shaft 311, a stop or pin 312, and a bushing 324, as shown in FIGS. 13-15. The second housing may include at least one groove 320, as shown in FIG. 14. Groove 320 may be configured to receive pin or stop 318 of first pivot structure 300a. Pivot shaft 311 may be received in bushing 324 and may pivotably connect (or pivotably mount) second pivot structure 302 to frame 301 to allow second pivot structure 302 to pivot relative to frame 301 about second pivot axis B. Pin 312 may be configured to be received in a groove of second pivot structure 302 (further discussed below).

Second pivot structure 302 may include any suitable structure configured to allow a user to pivot instrument assembly 600 about second pivot axis B, as shown in FIG. 4. For example, second pivot structure 302 may be pivotably connected to frame 301 via pivot shaft 311 and/or be configured to pivot relative to frame 301 about the second pivot axis. The second pivot structure may be disposed within gap 301d of frame 301 and include one or more portions that extend beyond and/or through the gap and frame 301 over a range of pivot positions about the second pivot axis. For example, handle 306, arm grip 307, and/or channel 326 may extend beyond gap 301d and frame 301.

Figure 17:
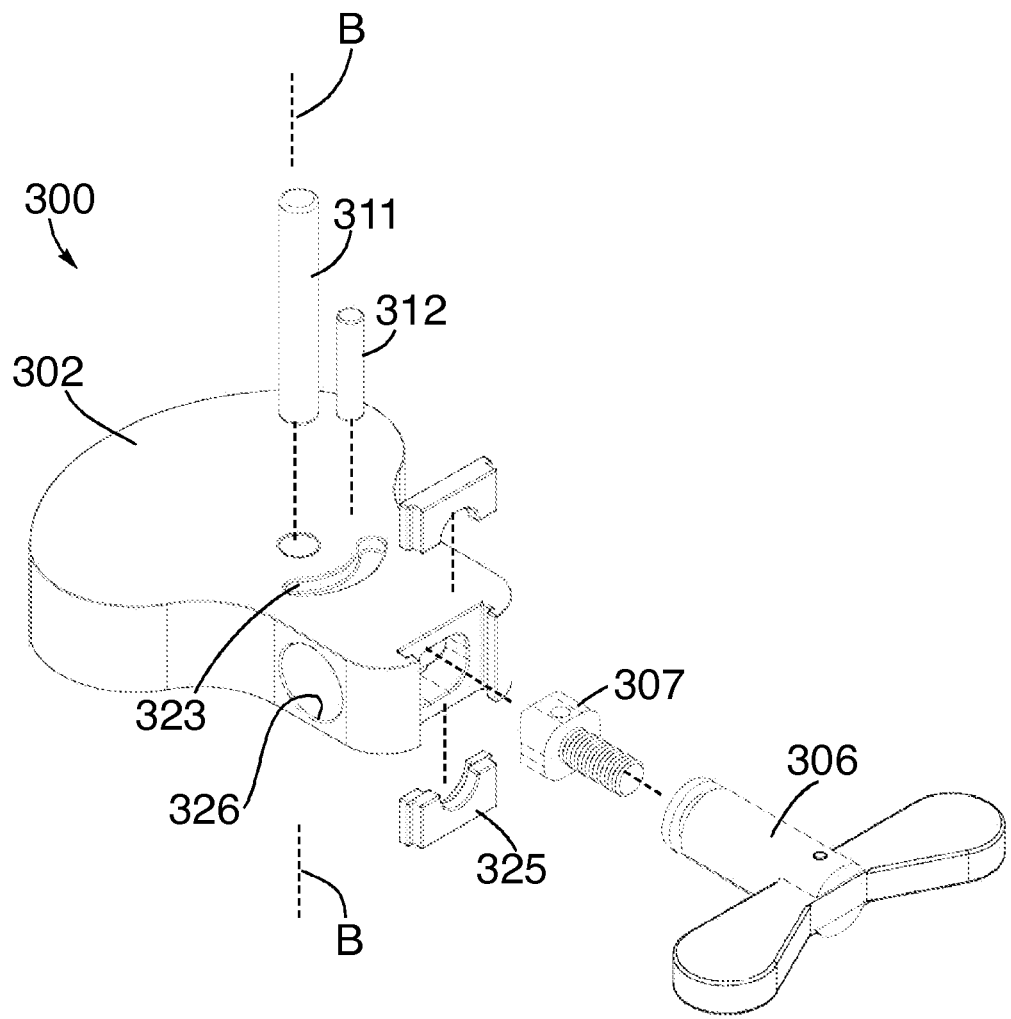
FIG. 17 is an exploded view of a second pivot structure of the pivot assembly of FIG. 13.
Figure 21:
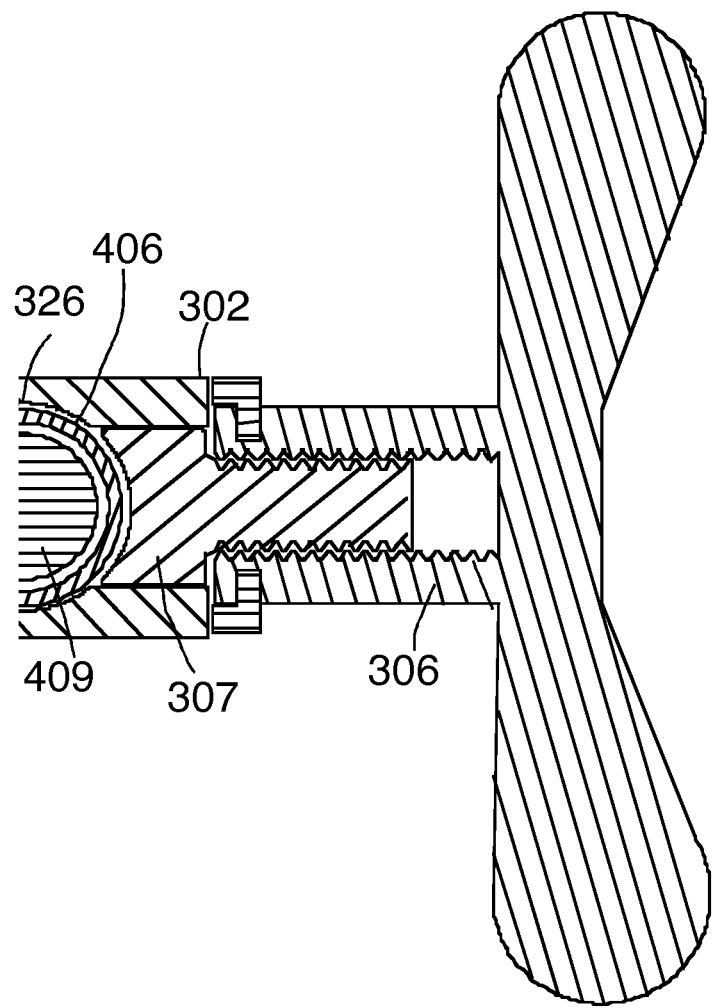
FIG. 21 is a partial view of the pivot assembly of FIG. 19, showing a second portion of the pivot assembly of the instrument assembly support apparatus of FIG. 2.
Figure 22:
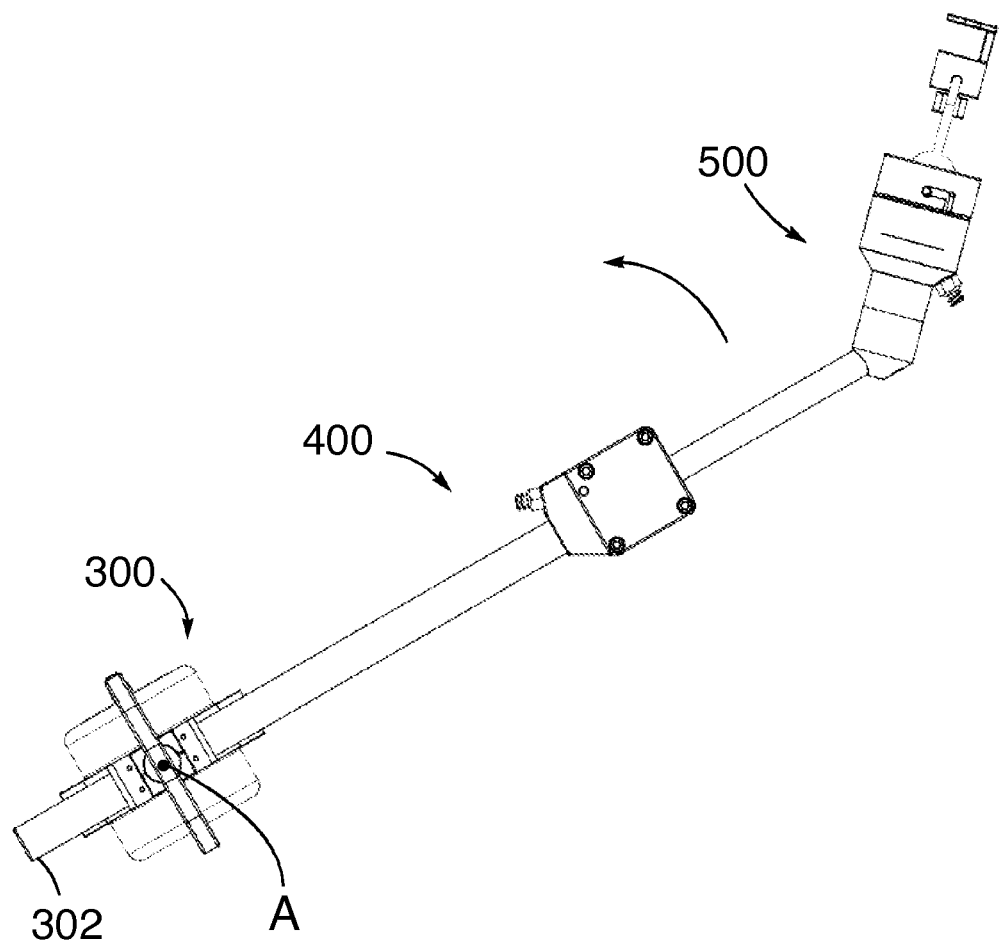
FIG. 22 is a partial front view of the instrument assembly support apparatus of FIG. 2, showing a support assembly of the instrument assembly support apparatus in a first position about a first pivot axis A.
Figure 23:
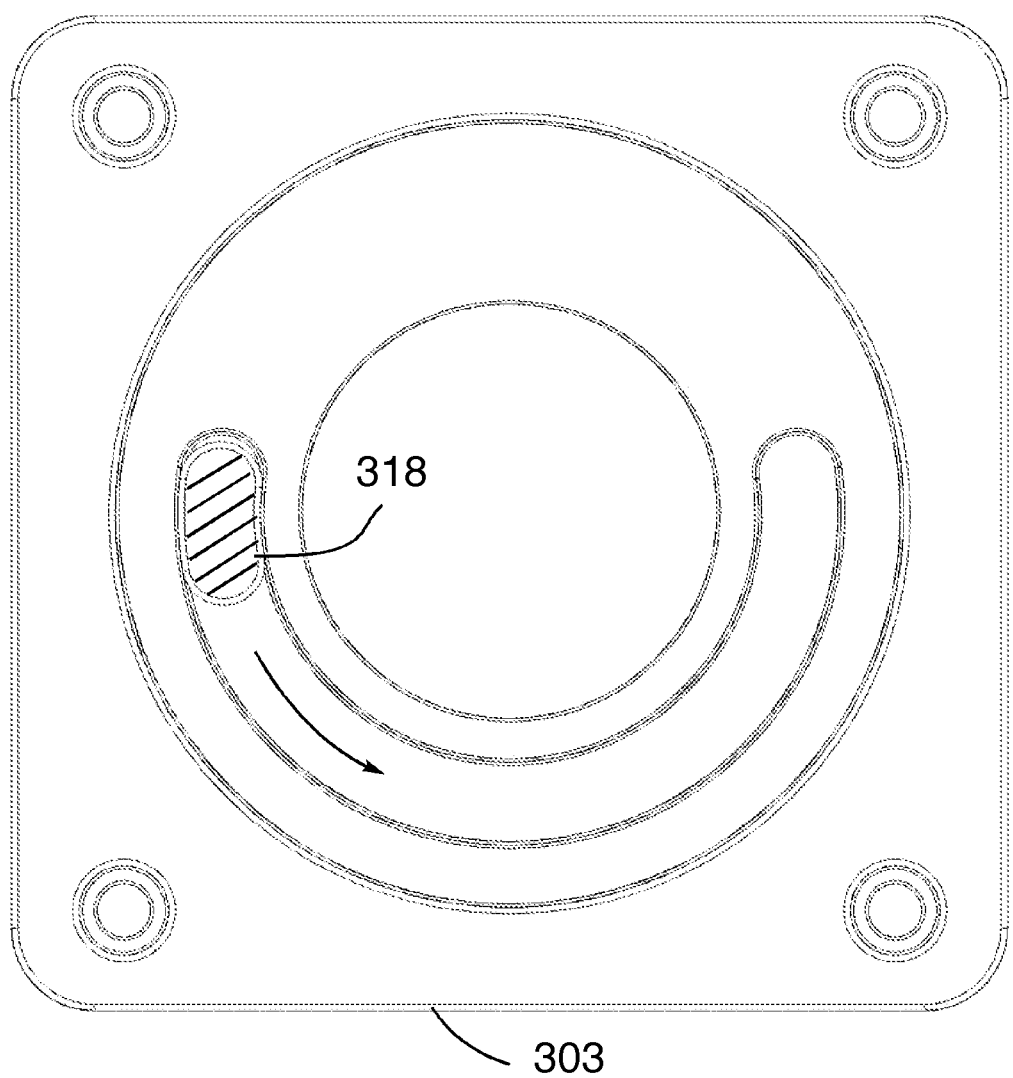
FIG. 23 is a partial cross-sectional view of the pivot assembly of FIG. 13 taken along lines 23-23 in FIG. 18, showing a stop adjacent a first end portion of a groove when the support assembly is in the first position shown in FIG. 22.
Figure 24:
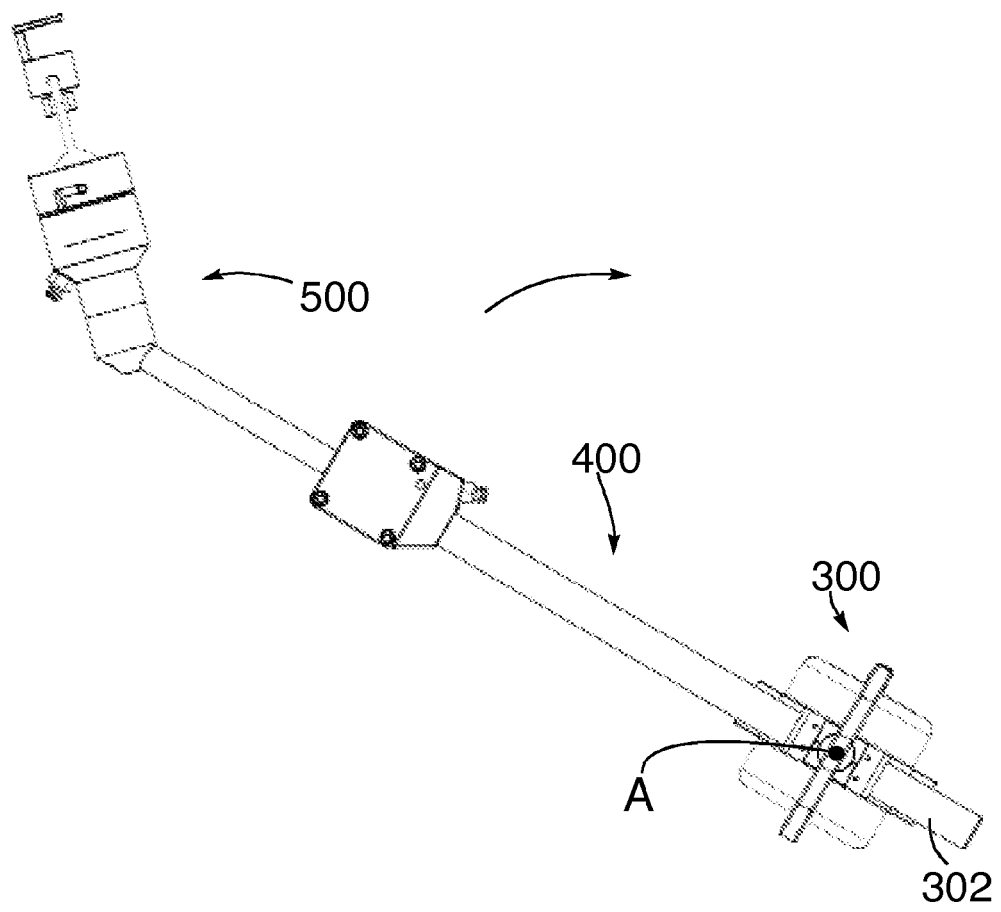
FIG. 24 is a partial front view of the instrument assembly support apparatus of FIG. 2, showing a support assembly of the instrument assembly support apparatus in a second position about a first pivot axis A.
Figure 25:
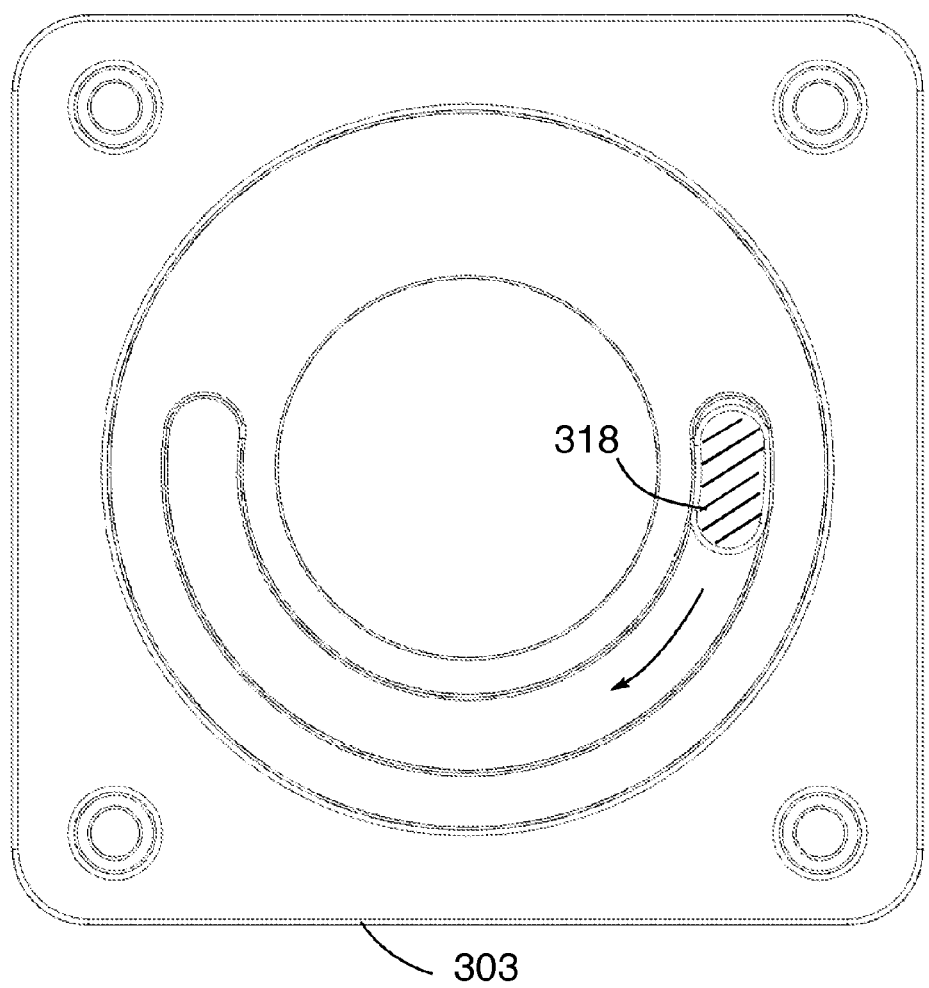
FIG. 25 is a partial cross-sectional view of the pivot assembly of FIG. 13 taken along lines 23-23 in FIG. 18, showing a stop adjacent a second end portion of a groove when the support assembly is in the second position shown in FIG. 24.
Figure 26:
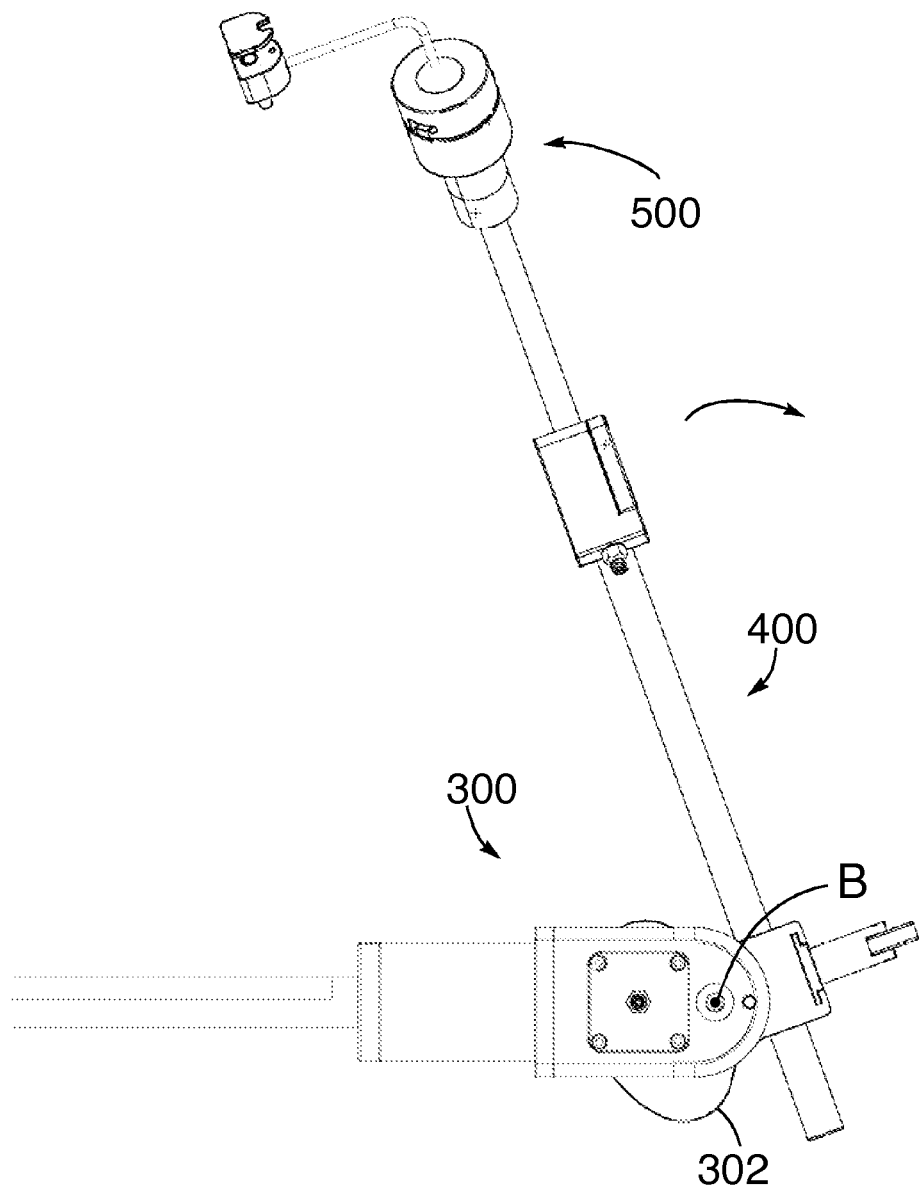
FIG. 26 is a partial side view of the instrument assembly support apparatus of FIG. 2, showing a support assembly of the instrument assembly support apparatus in a third position about a second pivot axis B.
Figure 27:
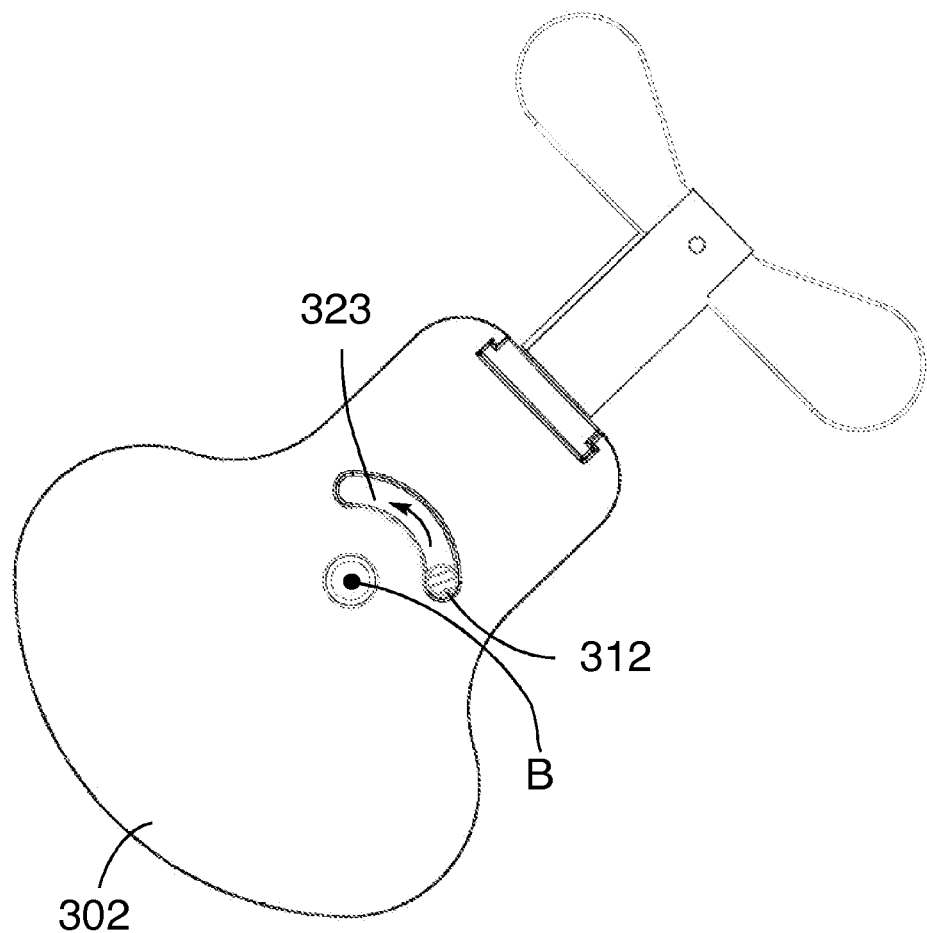
FIG. 27 is a top view of a second pivot structure and a pin of the pivot assembly of FIG. 13, showing the pin adjacent a first end portion of a groove of the second pivot structure when the support assembly is in the third position shown in FIG. 26.
Figure 28:
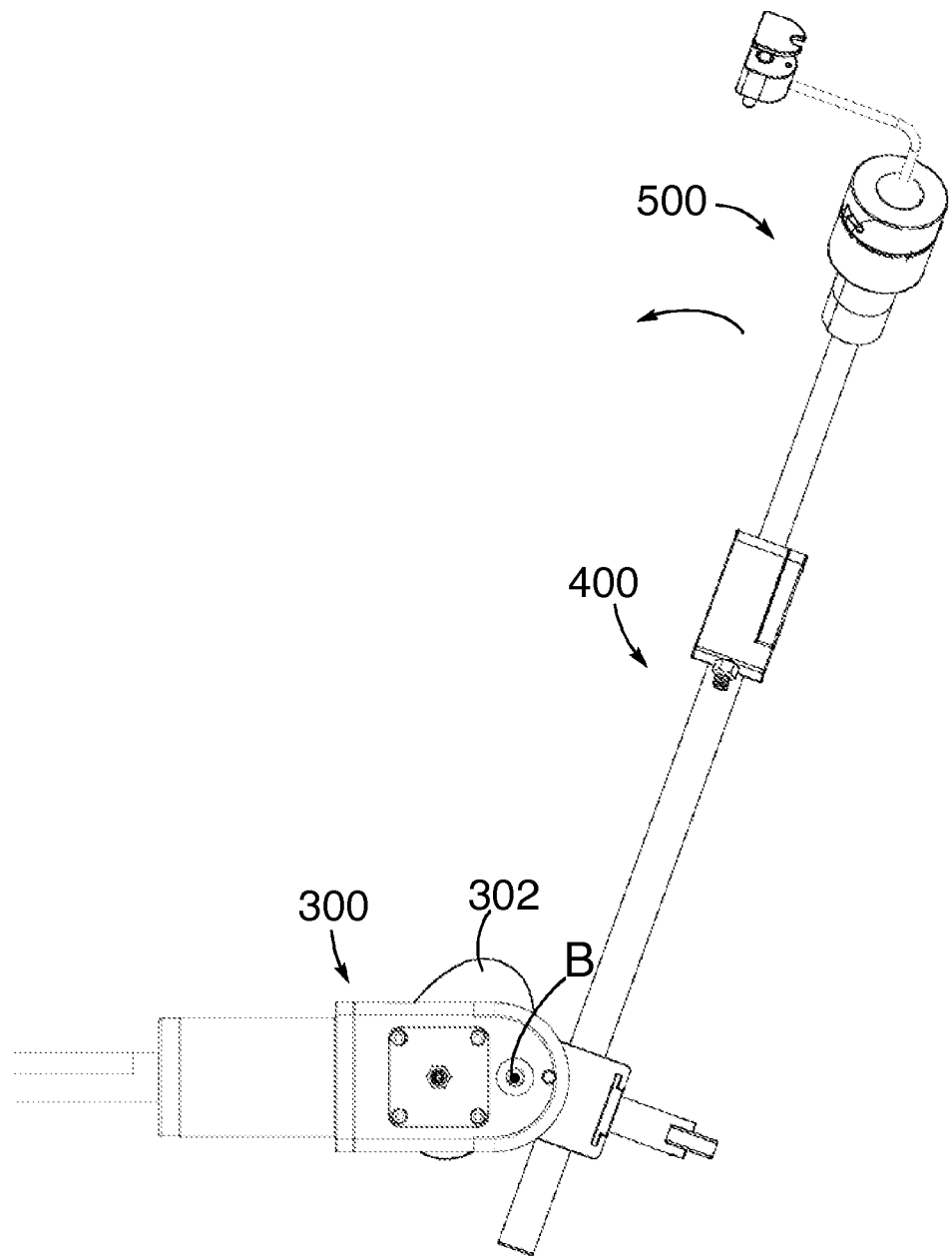
FIG. 28 is a partial side view of the instrument assembly support apparatus of FIG. 2, showing a support assembly of the instrument assembly support apparatus in a fourth position about a second pivot axis B.
Figure 29:
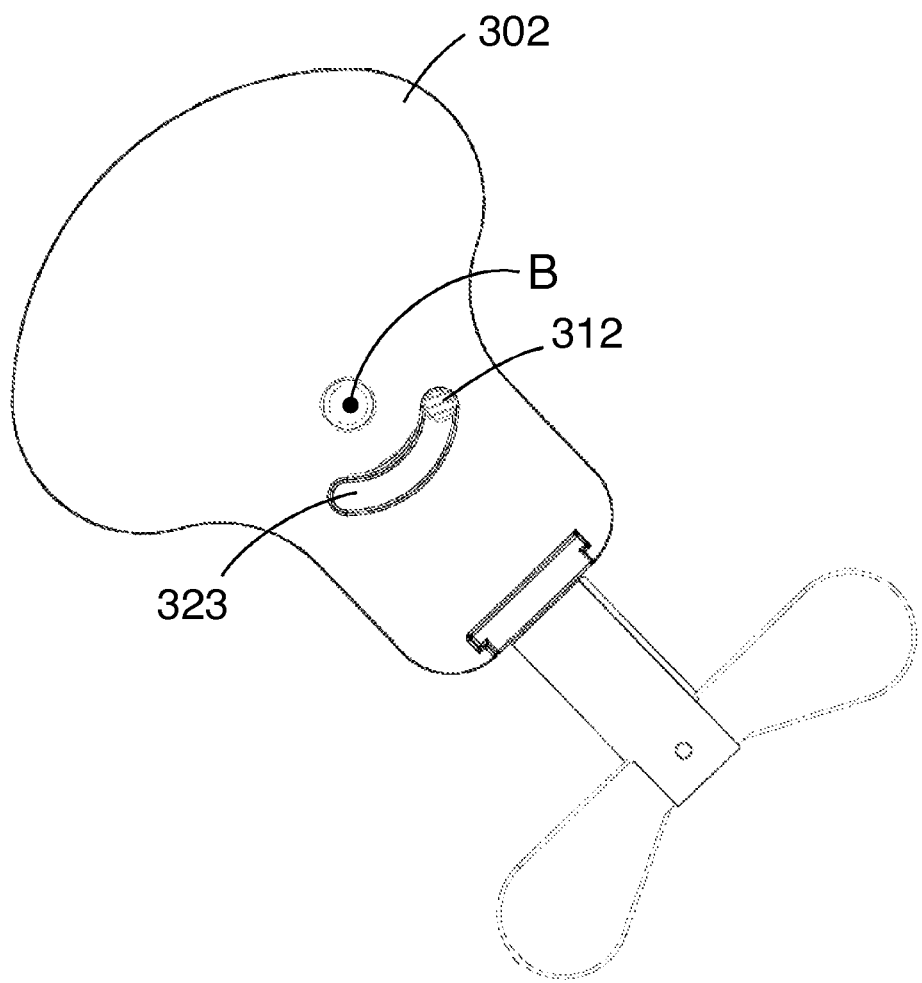
FIG. 29 is a top view of a second pivot structure and a pin of the pivot assembly of FIG. 13, showing the pin adjacent a second end portion of a groove of the second pivot structure when the support assembly is in the fourth position shown in FIG. 28.

Second pivot structure may, for example, include a handle 306, an arm grip 307, a groove 323, a handle retainer 325, and a channel 326, as shown in FIG. 17. Groove 323 may receive pin 312 of frame 301 and be configured to limit pivoting of second pivot structure 302 relative to frame 301 within any suitable predetermined number of degrees, such as ninety degrees. Alternatively, frame 301 may include a groove and second pivot structure 302 may include a pin received in that groove. Channel 326 may receive one or more components of sliding assembly 400, as further discussed below. During attachment of sliding assembly 400 to pivot assembly 300, component(s) of the sliding assembly, such as a first portion, may be inserted into channel 326. Handle 306 may be rotated to cause arm grip 307 to secure the component(s) of the sliding assembly.

FIGS. 22-29 illustrate movement of the instrument assembly support apparatus about the first and second pivot axes, and limiting of that movement via the pins and grooves described above. The first and second pivot axes may be along any suitable axes. For example, second pivot axis B may be perpendicular, orthogonal, or transverse to first pivot axis A (such as when viewed from a plane parallel to those axes). The axes may be referred to as being perpendicular even if they do not intersect. Although the first and second pivot axes are shown to be perpendicular to each other, the first and second pivot axes may have any suitable relationship to each other, and may or may not intersect. For example, the second pivot axis may be at a 45-degree angle relative to the first pivot axis. Additionally, although the first and second pivot axes are shown to have particular orientations, the first and second pivot axes may have any suitable orientations.

Although the frame and the first and second pivot structures are shown to include specific structure, any suitable structure configured to allow a user to pivot instrument assembly 600 about any suitable pivot axis or axes may be used. Additionally, although pivot assembly 300 is shown to include two pivot structures, the pivot assembly may include more or less pivot structures.

Sliding assembly (or arm assembly) 400 may include any suitable structure configured to allow a user to slide instrument 300 along a longitudinal axis C. For example, sliding assembly 400 may include a first portion 406 and a second portion 409, as shown in FIGS. 30-34. The first portion may be mounted to the pivot assembly, such as via the second pivot structure, for pivoting relative to frame 301 while the second portion may extend along or be spaced from the first portion.

In some embodiments, first portion 406 may include an outer arm, while second portion 409 may include an inner arm configured to slide within the outer arm and to pivot about longitudinal axis C relative to the outer arm, as shown in FIG. 4. Outer arm 406 may include any suitable structure configured to be received or mounted to the second pivot structure, and/or to support the inner arm. Inner arm 409 may include any suitable structure configured to be mounted relative to the outer arm. For example, the inner arm may slide within the outer arm and/or may connect to support assembly 500. The inner and outer arms may be reversed. The sliding assembly also may include an inner arm retainer (not shown) configured to prevent a user from removing inner arm 409 from outer arm 406.

Additionally, sliding assembly 400 may include a frame or housing 401. First portion 406 may support frame 401 and the second pivot structure may support the first portion. Although the outer and inner arms are shown to have a circular cross-section, the outer and inner arms may have any suitable cross-section(s) (such as oval, square, triangular, and rectangular cross-sections) configured to allow a user to slide the instrument along any suitable direction(s). Additionally, although sliding assembly 400 is shown to include outer and inner arms, any suitable structure configured to allow a user to slide instrument assembly 600 may be used. Moreover, although sliding assembly is shown to allow a user to slide the instrument assembly along directions perpendicular or orthogonal to the first and/or second pivot axes (such as when view from a plane parallel to those axes), the sliding assembly may be configured to allow a user to slide the instrument assembly along any suitable direction(s).

Figure 35:
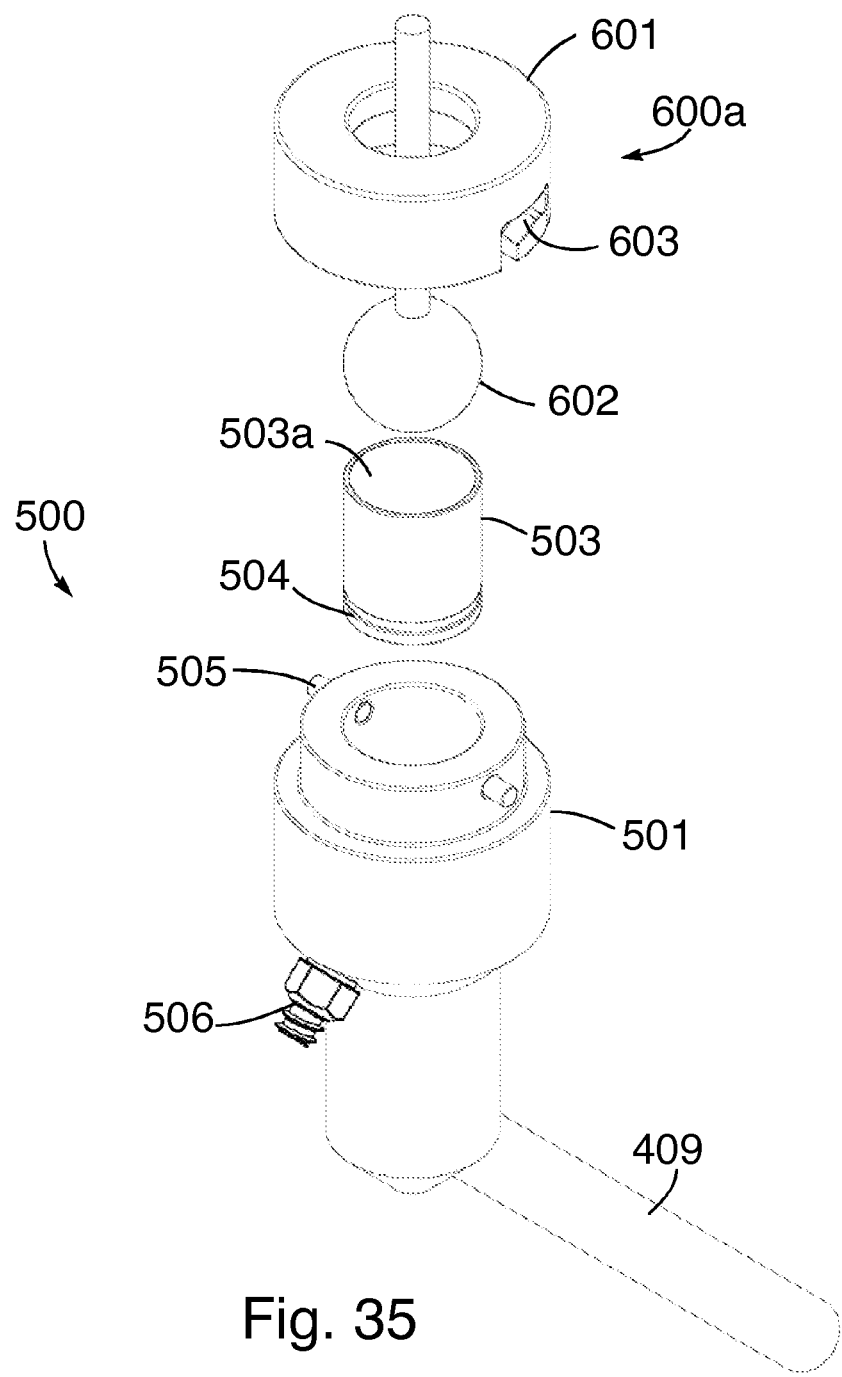
FIG. 35 is an exploded view of a support assembly of the instrument assembly support apparatus of FIG. 2, showing a partial view of an instrument assembly attached to the support assembly.
Figure 38:
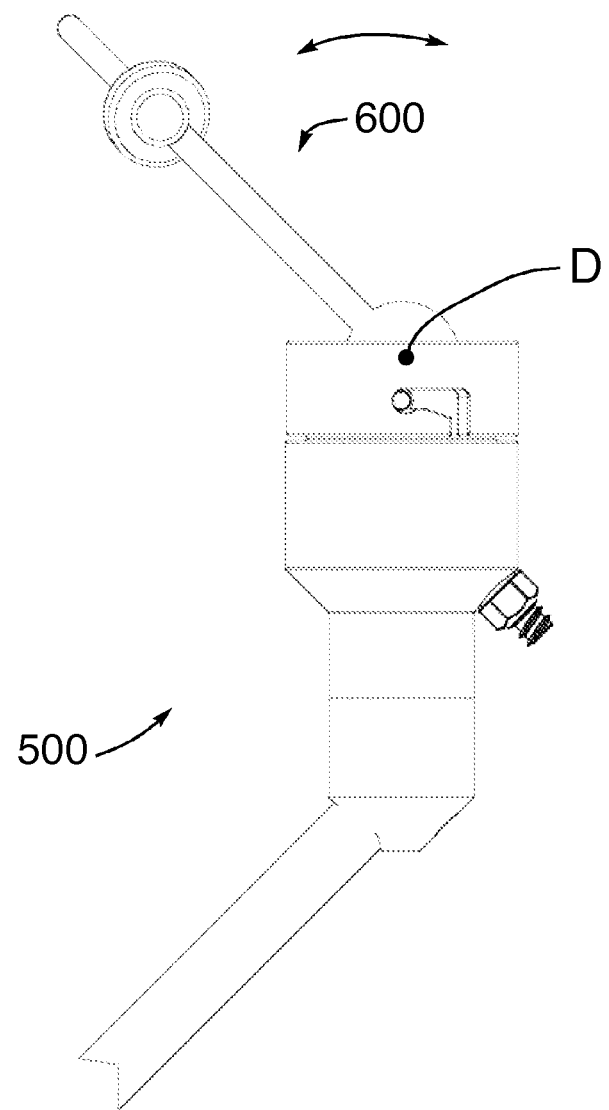
FIG. 38 is a front view of the support assembly of FIG. 35, showing an instrument assembly in a first position about an axis D.
Figure 39:
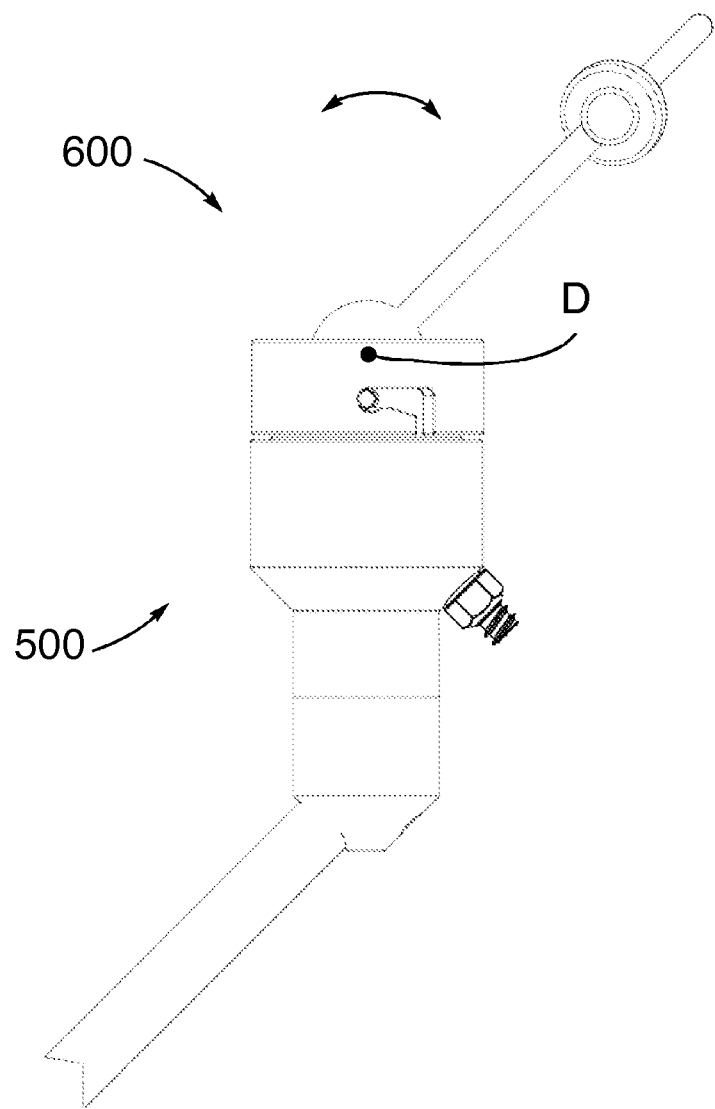
FIG. 39 is a front view of the support assembly of FIG. 35, showing an instrument assembly in a second position about an axis D.
Figure 40:
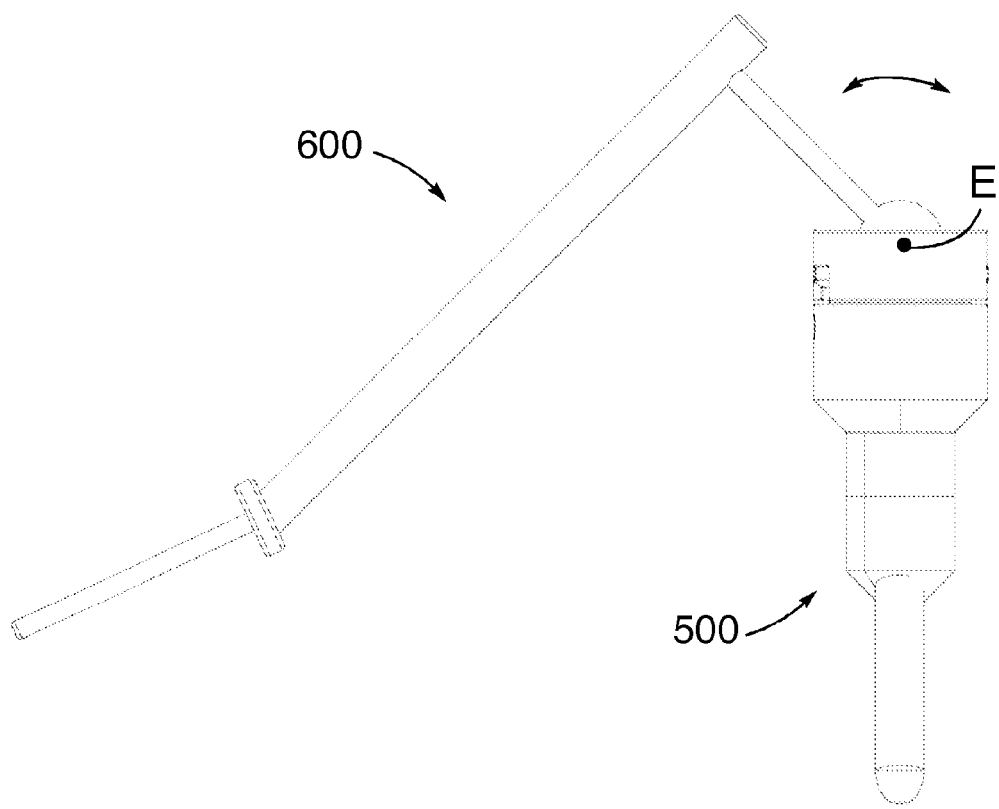
FIG. 40 is a side view of the support assembly of FIG. 35, showing an instrument assembly in a third position about an axis E.
Figure 41:
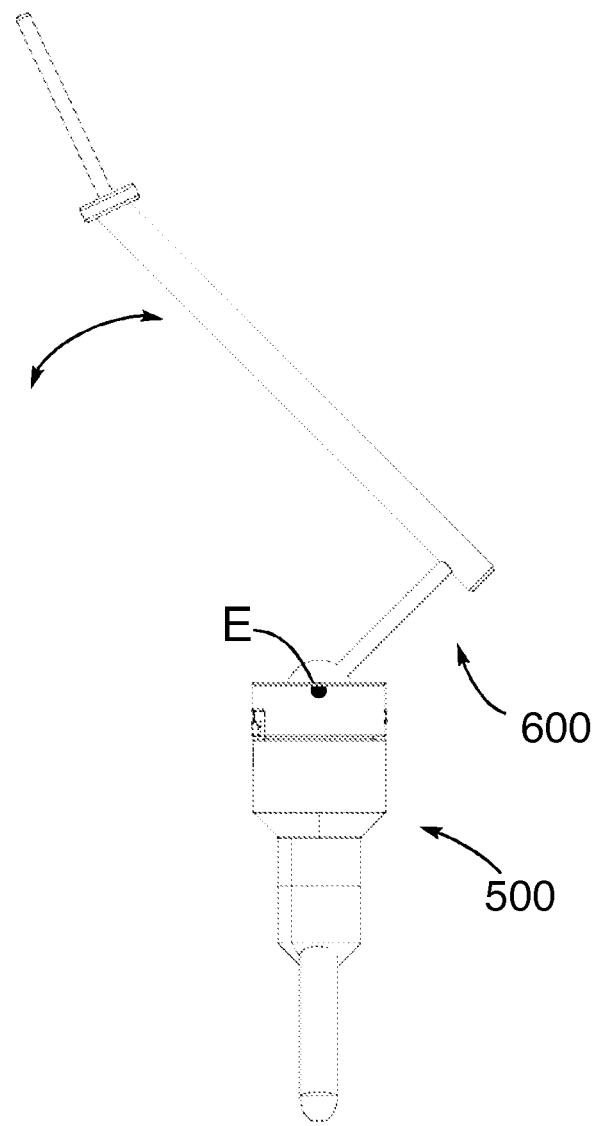
FIG. 41 is a side view of the support assembly of FIG. 35, showing an instrument assembly in a fourth position about an axis E.
Figure 42:
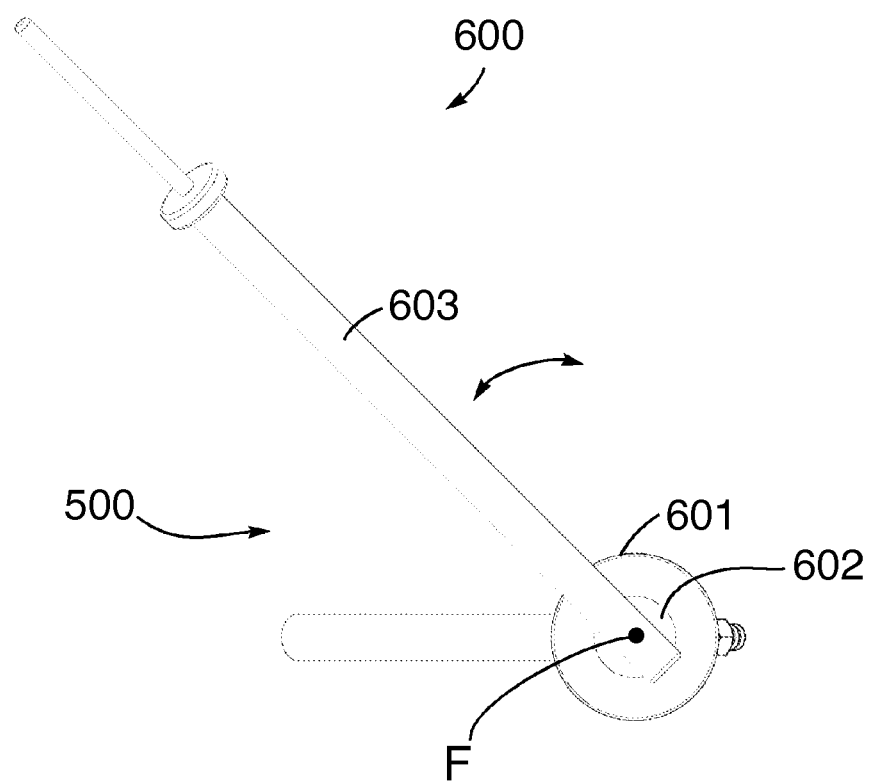
FIG. 42 is a top view of the support assembly of FIG. 35, showing an instrument assembly in a fifth position about an axis F.
Figure 43:
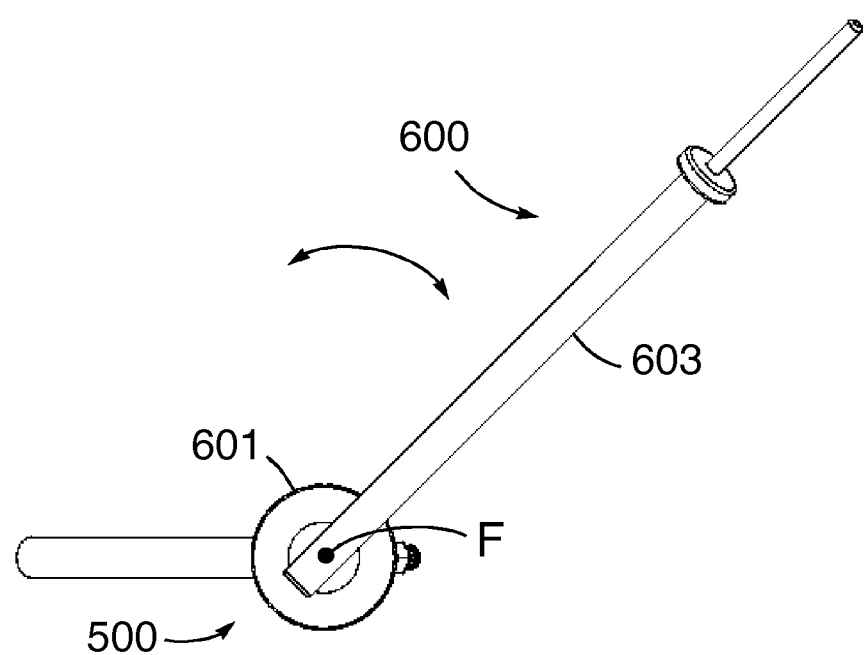
FIG. 43 is a top view of the support assembly of FIG. 35, showing an instrument assembly in a sixth position about an axis F.
Figure 44:
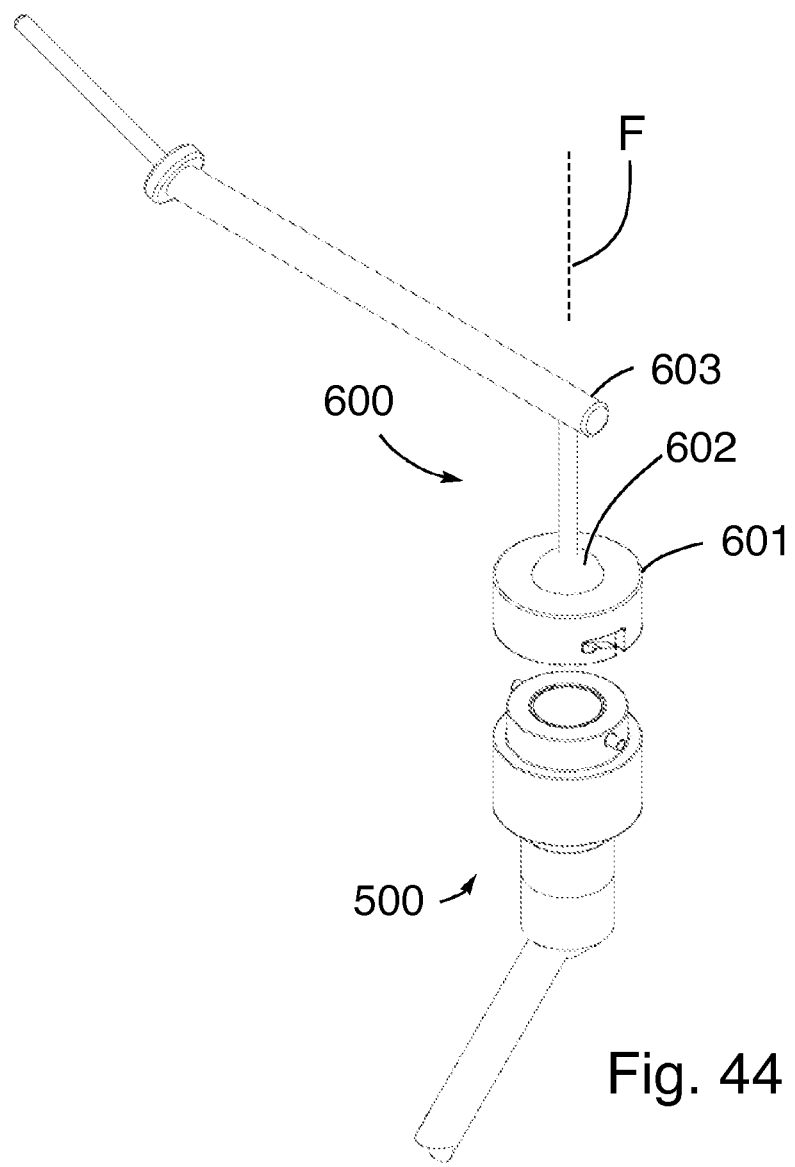
FIG. 44 is an isometric view of the support assembly of FIG. 35, showing an instrument assembly detached from the support assembly.
Figure 45:
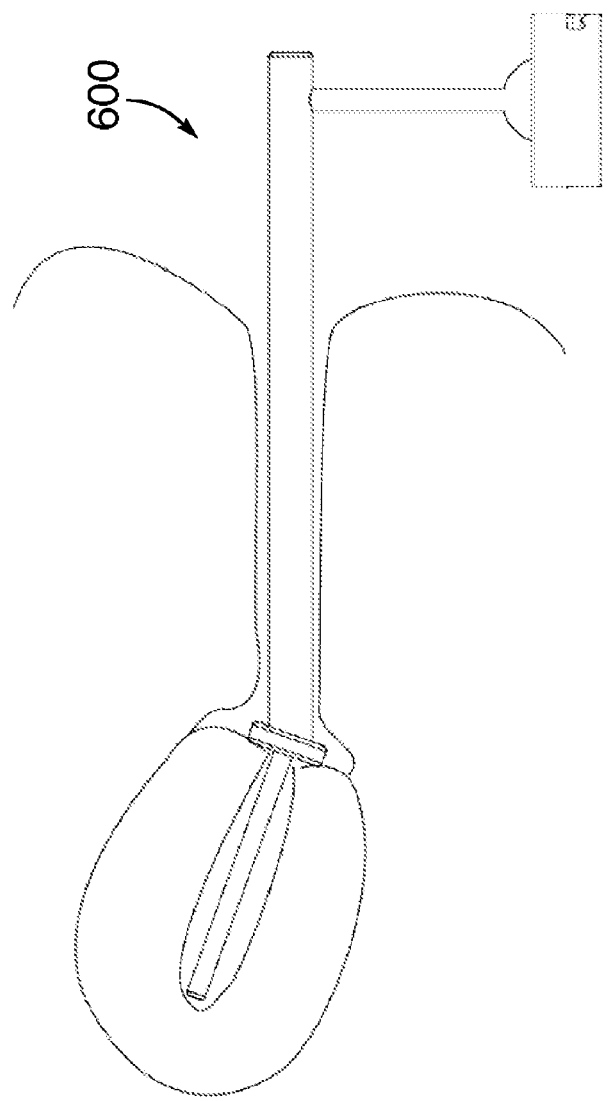
FIG. 45 is a schematic view of an instrument assembly inserted into a uterus while the instrument assembly is supported by the instrument assembly support apparatus of FIG. 2.
Figure 46:
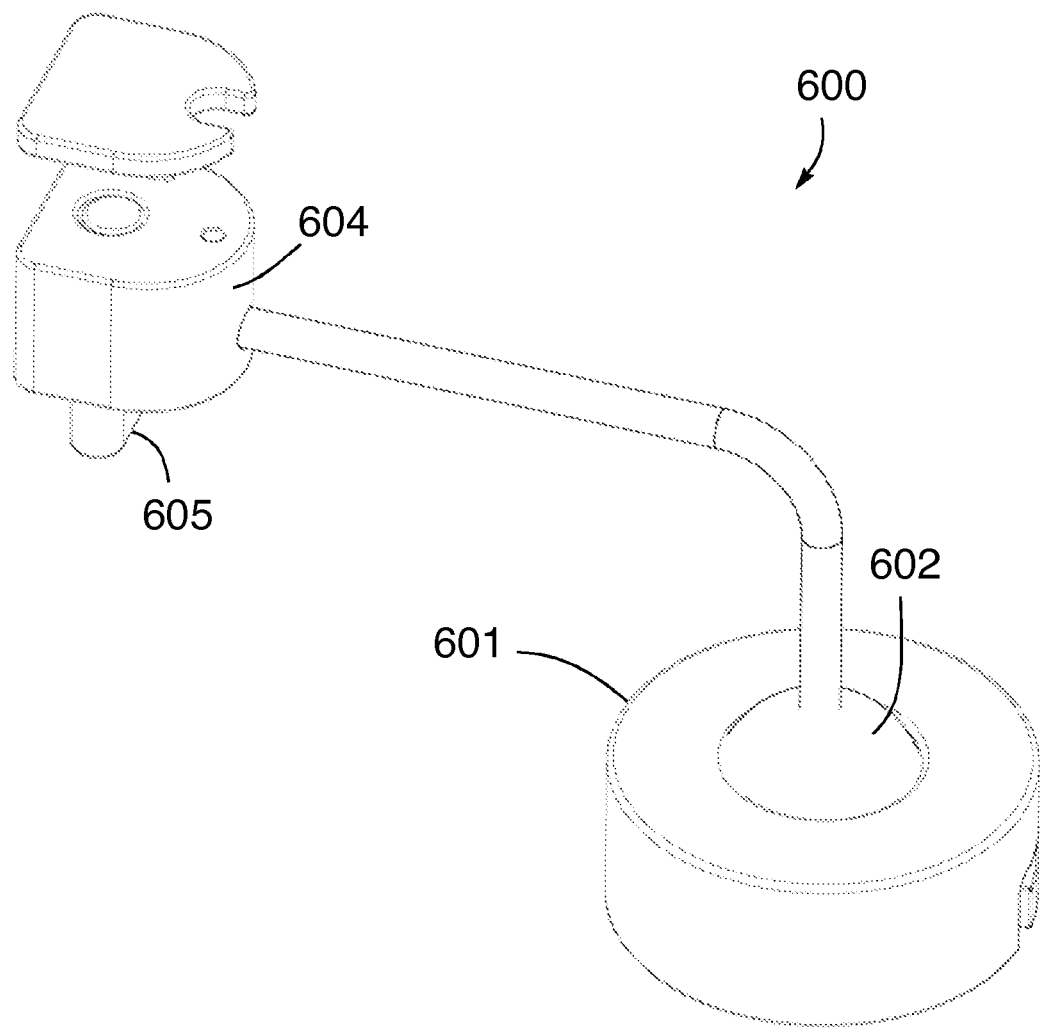
FIG. 46 is an isometric view of another example of an instrument assembly.
Figure 47:
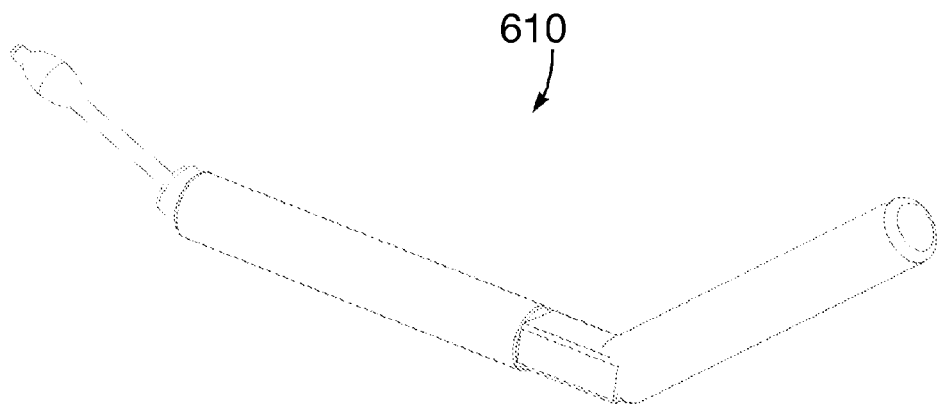
FIG. 47 is an isometric view of an example of an instrument that may be supported by the instrument assembly of FIG. 46.
Figure 48:
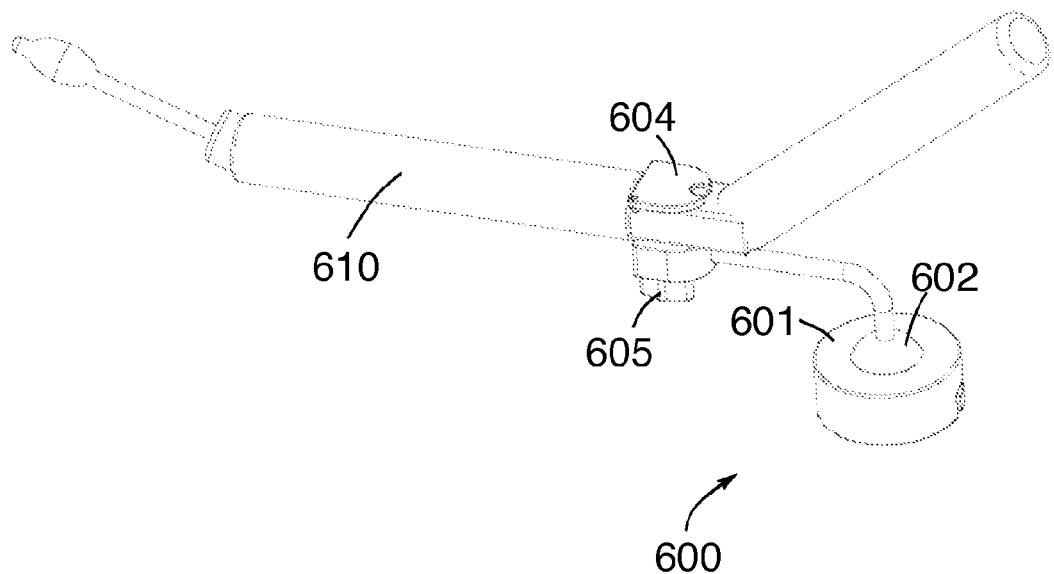
FIG. 48 is an isometric view of the instrument of FIG. 47 supported by the instrument assembly of FIG. 46.
Figure 49:
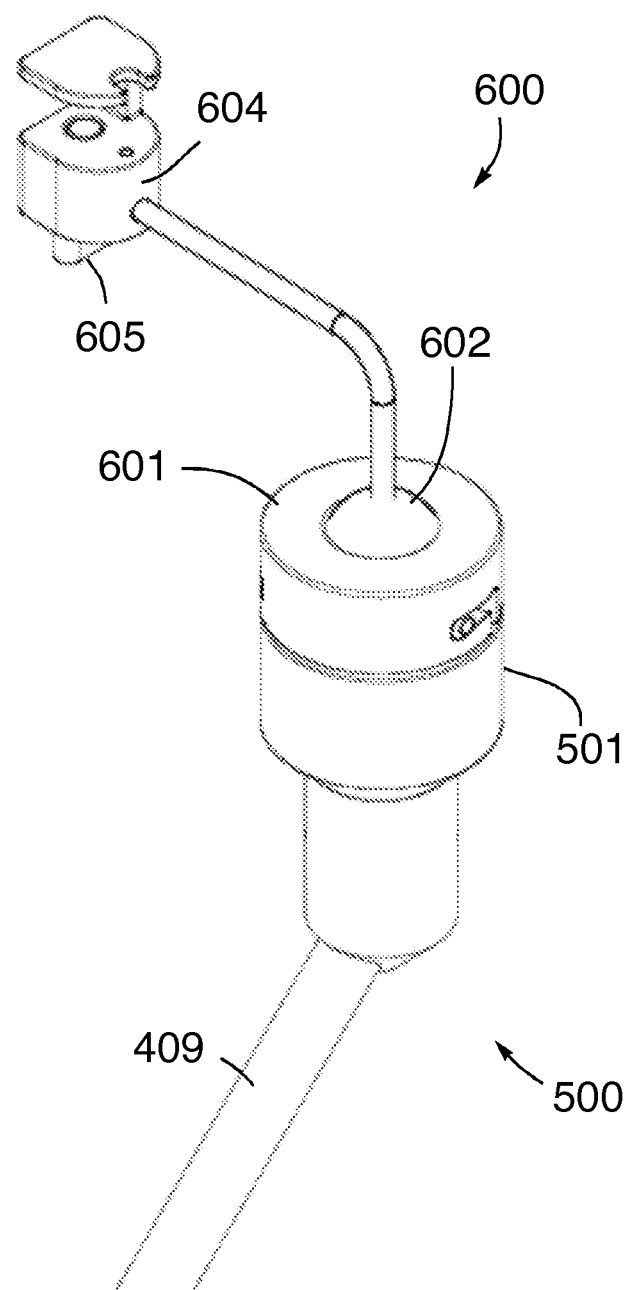
FIG. 49 is an isometric view of the support assembly of FIG. 35, showing the instrument of FIG. 47 attached to the instrument assembly of FIG. 46.
Figure 50:
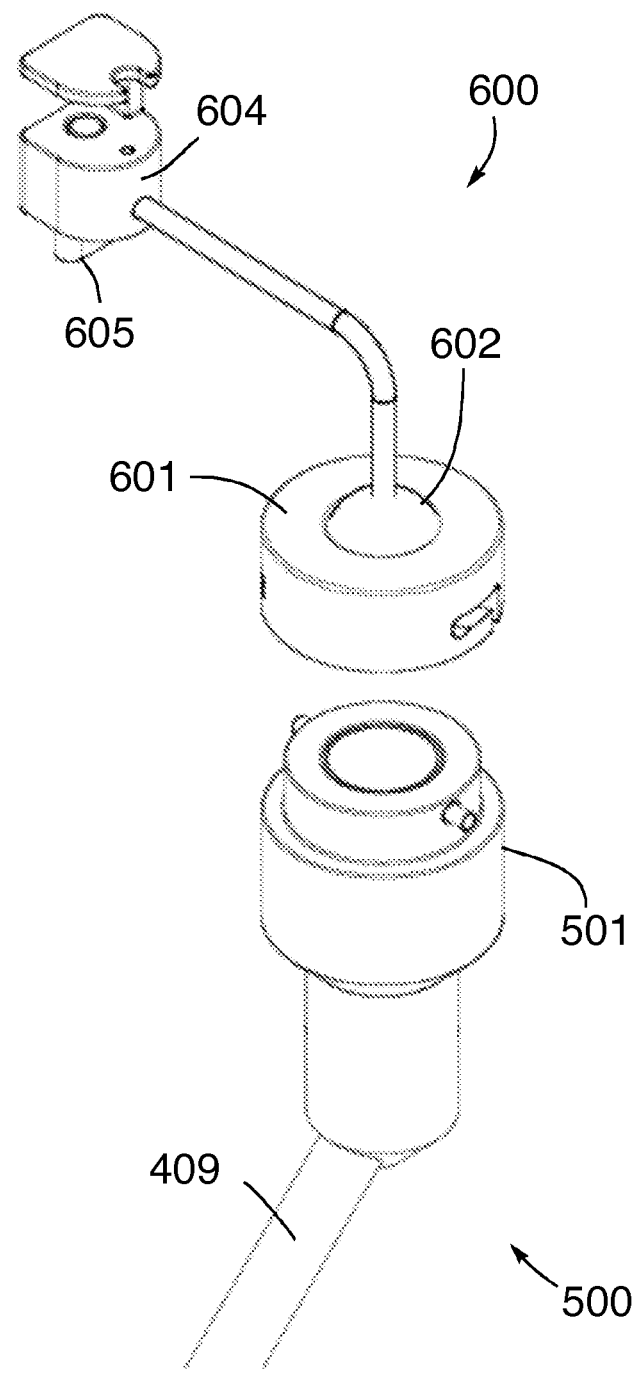
FIG. 50 is an isometric view of the support assembly of FIG. 35, showing the instrument of FIG. 47 detached from the instrument assembly of FIG. 46.
Figure 51:
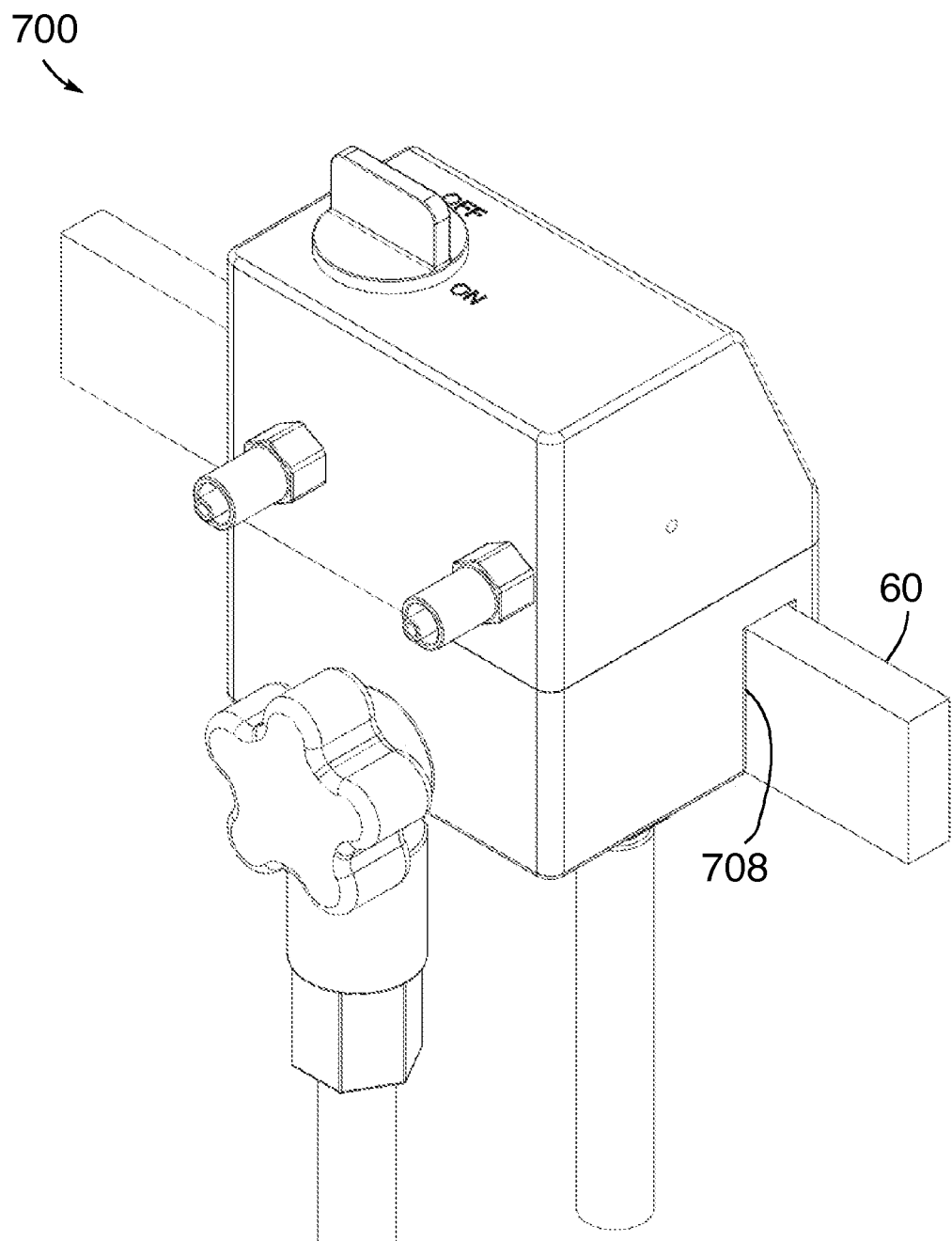
FIG. 51 is an isometric view of a gas supply assembly of the instrument assembly support apparatus of FIG. 2.
Figure 52:
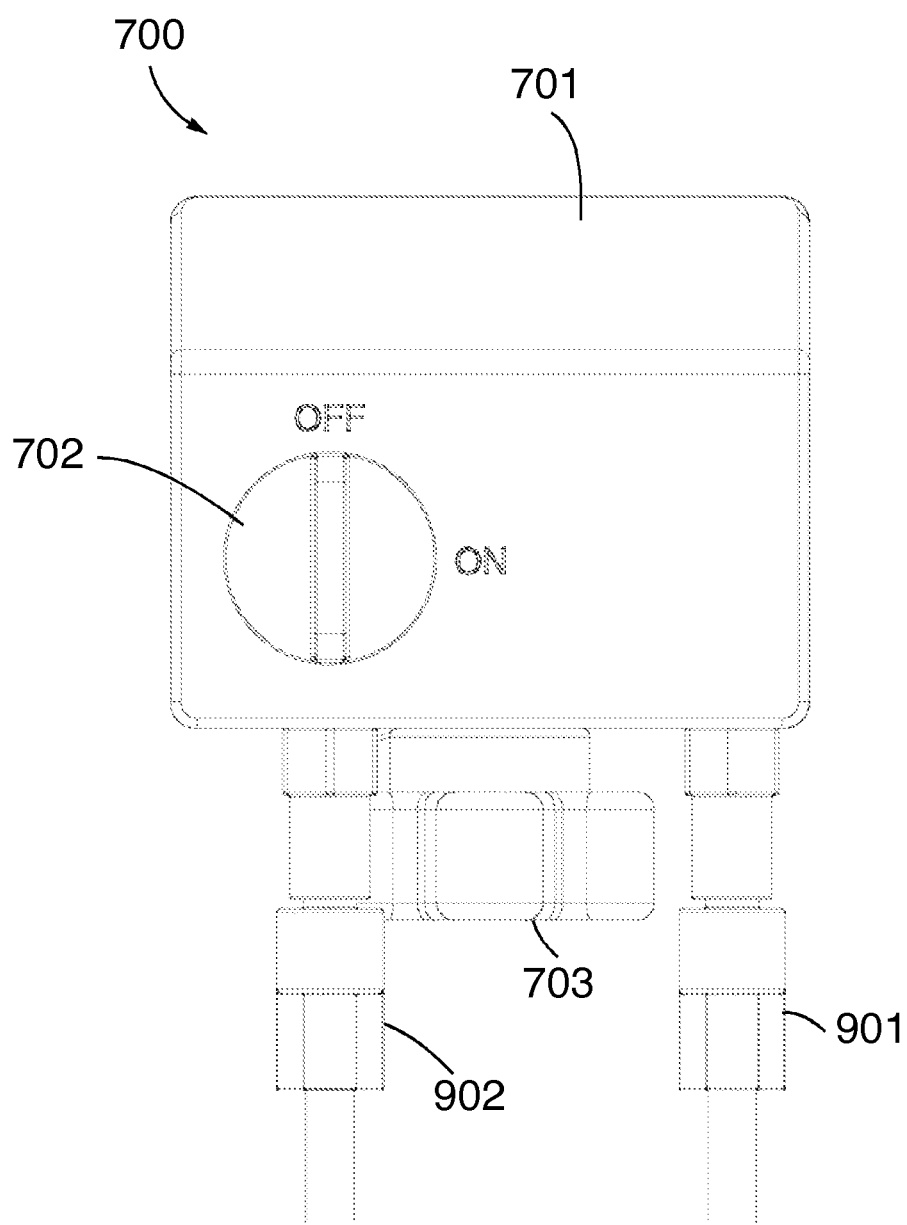
FIG. 52 is a top view of the gas supply assembly of FIG. 51, showing a switch in an "off" position.
Figure 53:
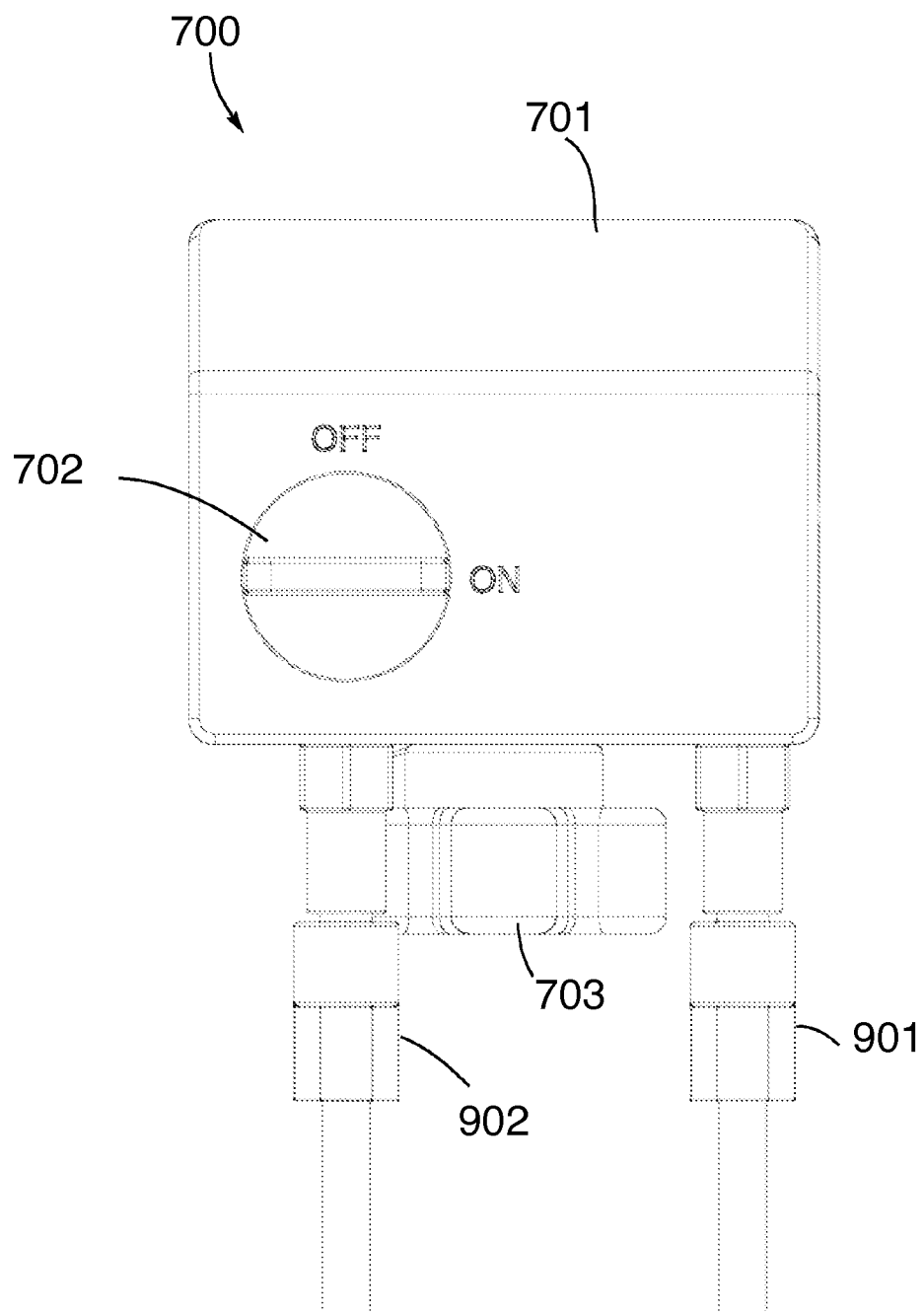
FIG. 53 is a top view of the gas supply assembly of FIG. 51, showing the switch of FIG. 52 in an "on" position.

The instrument assembly support apparatus also may include support assembly 500, which may include any suitable structure configured to support instrument assembly 600 and/or secure the instrument assembly to the instrument assembly support apparatus. For example, the support assembly may include a frame or housing 501 and at least one pin 505, as shown in FIGS. 35-37. The frame may be mounted to the second portion of the sliding assembly. Pin 505 may be configured to be received in a slot of instrument assembly 600, as further discussed below.

Instrument assembly support apparatus may be configured to support any suitable instrument assembly 600. The instrument assembly may include one or more instrument support arms, which may be support arms for one or more instruments and/or one or more instrument holders. Instrument assembly 600 may include a joint assembly 600a with any suitable structure configured to allow for movement of the instrument(s) and/or instrument holder(s) along one or more axes, such as axes D, E, and F shown in FIGS. 4 and 38-43.

For example, when joint assembly 600a includes a ball joint, the joint assembly may include a ball-retaining attachment cap 601 and a ball 602, as shown in FIGS. 35 and 37. The attachment cap may be configured to retain ball 602 against curvilinear face 503a (also may be referred to as a seat or a socket), and may include any suitable structure configured to mate with and/or attach to one or more components of support assembly 500, such as at least one slot 603 configured to receive pin 505 of the support assembly. An example of instrument assembly 600 in the form of a uterine manipulator is shown in FIGS. 35-45. Although instrument assembly 600 in those figures is shown to be in the form of a uterine manipulator, the instrument assembly may be in the form of any suitable instrument(s).

Another example of instrument assembly 600 in the form of an instrument holder, such as a uterine manipulator holder, is shown in FIGS. 46-50. In that example, instrument assembly 600 also may include a holder 604 and a grip handle 605. Holder 604 may be configured to receive one or more instruments, such as an instrument 610. Grip handle 605 may be configured to selectively secure instrument 610 to holder 604. Although instrument assembly 600 is shown in FIGS. 46-50 to include a particular type of holder 604 for a particular type of instrument 650, the instrument assembly may include any suitable holder(s) for any suitable type(s) of instruments.

Referring now to FIG. 1, instrument assembly support apparatus 70 also may include one or more lock assemblies 630, which may include any suitable structure configured to lock movement of instrument assembly 600. For example, lock assemblies 630 may include a first lock assembly 640 and a second lock assembly 650, as shown in FIGS. 14-15. Those lock assemblies may be mounted to or supported in any suitable location. For example, the lock assemblies may be supported via frame 301 of pivot assembly 300.

The first lock assembly may include any suitable structure configured to lock first pivot structure 300a and/or prevent a user from pivoting instrument assembly 600 about first pivot axis A. For example, first lock assembly 640 may include a first lock element 317, a second lock element 314, and first stops 315a and 315b, as shown in FIGS. 13-14.

First lock element 317 may include any suitable structure configured to fixedly be attached to shaft 305. For example, first lock element 317 may include a first planar face 317a. The second lock element may include any suitable structure configured to move toward the first planar face. For example, second lock element 314 may include a second planar face 314a. When second lock element 314 moves toward first lock element 317, second planar face 314a may contact first planar face 317a, thereby frictionally preventing frame 301 from pivoting relative to first lock element 317 and shaft 305.

Second lock element 314 may be positioned at any suitable location and/or disposed to move along any suitable direction relative to the first lock element. For example, the second lock element may be positioned opposite from the first lock element (such that the second face opposes the first face and both the first and second faces are intersected by the first pivot axis) and/or be disposed to move normal to the first lock element such that the second face of the second lock element engages the first face of the first lock element. The second face may include a circular or annular region or a group of spaced regions concentric with first pivot axis A.

Although the first and second lock elements are shown to include at least substantially circular discs and plates, those lock elements may be any suitable shape. Additionally, although the second lock element is shown to be disposed to move normal to the first lock element, that lock element may be disposed to move in any suitable direction. Moreover, although the second lock element is configured to move towards the first lock element, the first lock element may alternatively, or additionally, move towards the second lock element. Furthermore, although the second lock element is shown to be positioned such that the first pivot axis intersects the second lock element at a center of the second lock element, the second lock element may be positioned in any suitable location such that the first pivot axis intersects the second lock element at other location(s) of the second lock element, such as a perimeter or an end portion of the second lock element. In some embodiments, the second lock element may be positioned such that the first pivot axis does not intersect any portion of the second lock element.

First stops 315a and 315b may be configured to prevent pivoting of the second lock element about first pivot axis A. For example, the first stops may be attached to the second lock element in any suitable portion(s) of the second lock element and may be received in the frame in any suitable area(s), such as in apertures 321 of frame 301 (one of the apertures is shown in FIG. 16). Although the second lock element is shown to have two stops, any suitable number of stops may be used.

Second lock assembly 650 may include any suitable structure configured to lock second pivot structure 302 and/or prevent a user from pivoting instrument assembly 600 about second pivot axis B. For example, second lock assembly 650 may include a third lock element 313a and a fourth lock element 313b, as shown in FIG. 15. Second pivot structure 302 may be disposed between the third and fourth lock elements.

Third lock element 313a may include a third planar face 313a1. Fourth lock element 313b may include a fourth planar face 313b1, as shown in FIG. 15. The third and/or fourth lock elements may be positioned at any suitable location and/or disposed to move along any suitable direction relative to each other. For example, the third lock element may positioned opposite from the fourth lock element (such that the fourth face opposes the third face and second pivot axis B does not intersect any portion of the third and fourth lock elements) and/or be disposed to move normal toward each other such that the third face engages a fifth planar face 302a of second pivot structure 302 and the fourth face engages a sixth planar face 302b of the second pivot structure. Although the third and fourth lock elements are positioned such that second pivot axis B does not intersect those lock elements, the third and/or fourth lock elements may be positioned such that second pivot axis B does intersect the lock element(s) at their centers, perimeters, end portions, and/or any other locations.

Although first and second lock assemblies 640 and 650 are shown to include particular structure, the first and/or second lock assemblies may alternatively, or additionally, include one or more components that are the same as or similar to the components of any of the other lock assemblies described in this disclosure. Additionally, or alternatively, the first and/or second lock assemblies may include one or more components of the locking assemblies disclosed in U.S. Pat. Nos. 5,957,423 and 7,670,281, the complete disclosures of which are hereby incorporated by reference for all purposes.

Lock assemblies 630 also may include a biasing mechanism 690, which may include any suitable structure configured to selectively bias the second lock element toward the first lock element, and/or the third and fourth lock elements toward second pivot structure, as shown in FIG. 3. For example, biasing mechanism 690 may include a gas supply assembly 700, a pedal assembly 800, and a first receiving assembly 850, as shown in FIGS. 3, 13-16, 20 and 51-57.

Gas supply assembly 700 may include a housing 701, a switch 702, an attachment knob 703, a gas inlet line 704, gas/pedal lines 705 and 706, a cover hose 707, a groove 708, and gas outlet lines 901 and 902, as shown in FIGS. 3 and 51-57. Switch 702 may be configured to allow a user to selectively connect pressurized gas supply 903 via gas inlet line 704 to other components of the gas supply assembly. The pressurized gas supply may include any suitable supply such as a pressurized gas cylinder or tank of nitrogen or air.

Figure 54:
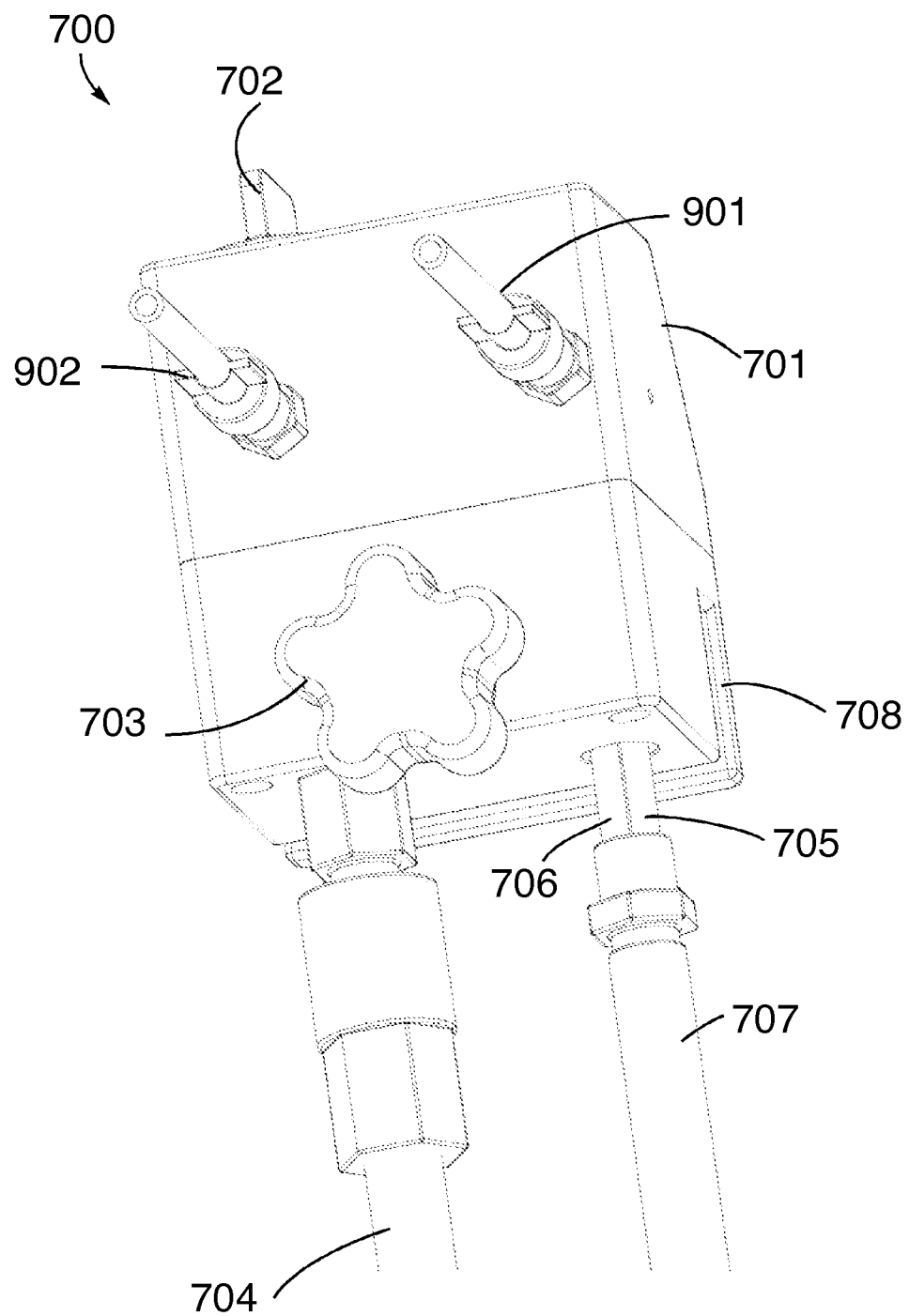
FIG. 54 is an isometric bottom view of the gas supply assembly of FIG. 51.
Figure 55:
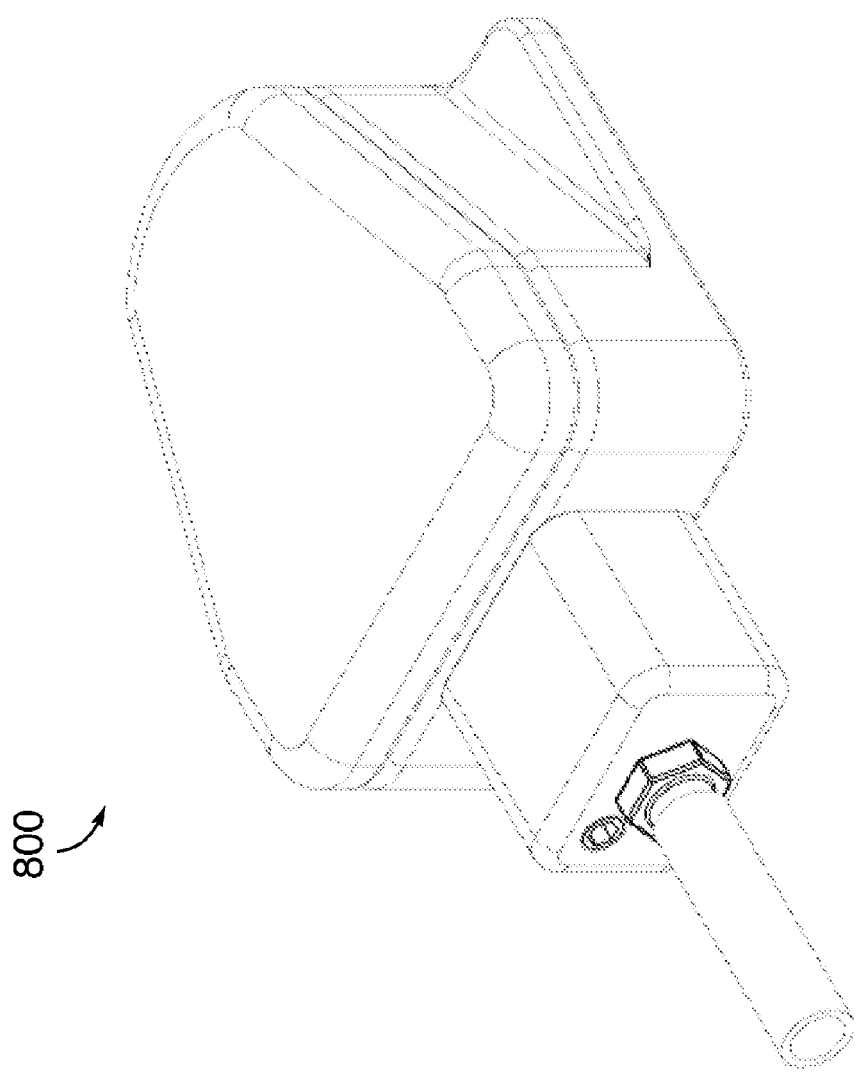
FIG. 55 is an isometric view of a pedal assembly of the instrument assembly support apparatus of FIG. 2.
Figure 56:
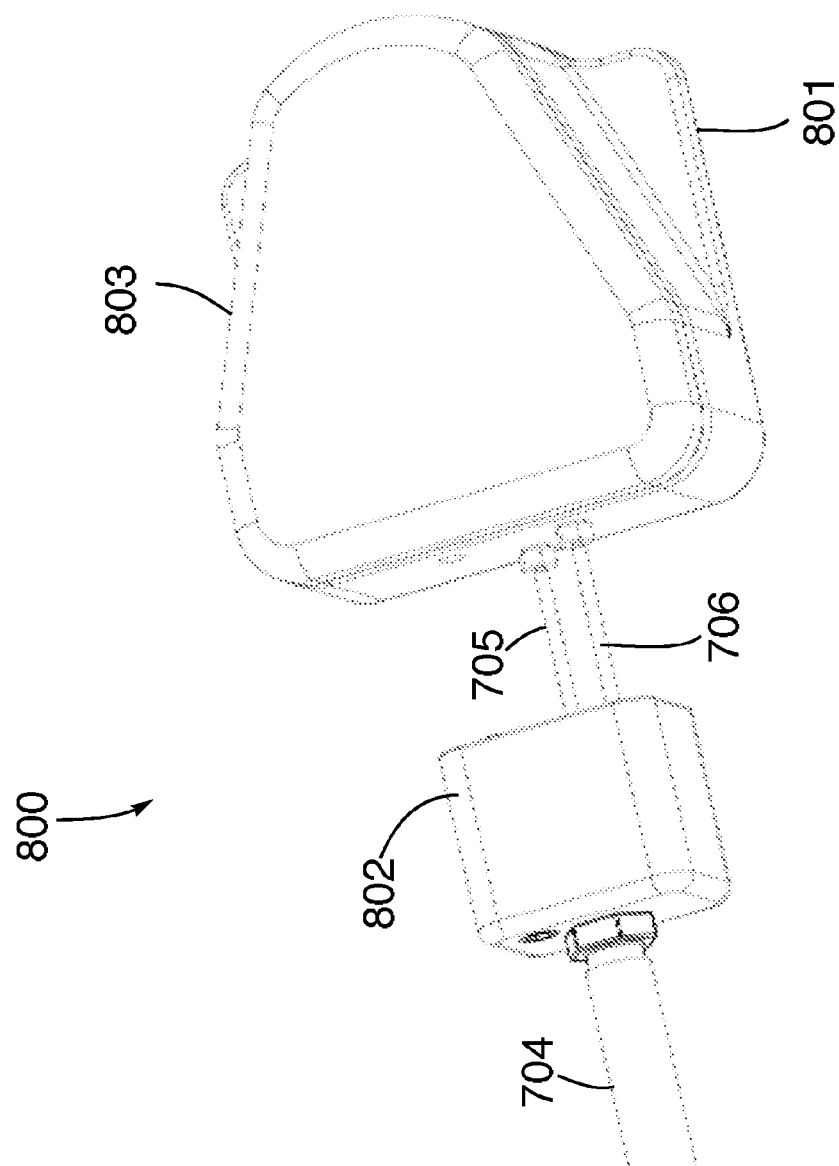
FIG. 56 is an isometric view of the pedal assembly of FIG. 55, showing gas/pedal lines attached to the pedal assembly.

Gas/pedal lines 705 and 706 may fluidly connect gas supply assembly 700 to pedal assembly 800. Those lines may be contained in cover hose 707, as shown in FIG. 54. Groove 708 may be configured to be received in external frame 80, while attachment knob 703 may configured to allow a user to secure the gas supply assembly to the external frame. Gas outlet line 901 may fluidly connect the gas supply assembly to the third and/or fourth lock assemblies, as further discussed below. Gas outlet line 902 may fluidly connect the gas supply assembly to the first and second lock assemblies. Although gas supply assembly 700 is shown to include two gas outlet lines 901 and 902, the gas supply assembly may include more gas outlet lines (for example, a single gas outlet line for each lock assembly) or fewer gas outlet lines (for example, a single gas outlet line for the first, second, third, and/or fourth lock assemblies).

Pedal assembly 800 may include any suitable structure configured to remotely actuate and/or selectively control the flow of (and/or regulate the pressure of) the pressurized gas from the gas inlet line to the lock assembly(ies). For example, the pedal assembly may include a base 801, a line cover 802 attached to cover hose 707, and a foot pedal 803. Although biasing mechanism 690 is shown to include a pedal assembly, the biasing mechanism may alternatively, or additionally, include remote actuators located in any suitable location, such as on the support assembly or on the instrument assembly. Illustrative examples of remote actuators are disclosed in U.S. Pat. Nos. 5,957,423 and 7,670,281, the complete disclosures of which are hereby incorporated by reference for all purposes.

First receiving assembly 850 may include any suitable structure configured to receive pressurized gas and urge (1) the second face and/or the second lock element toward the first face and/or the first lock element, and/or (2) the third face and/or the third lock element and the fourth face and/or fourth lock element toward the fifth and sixth faces and/or the second pivot structure. For example, the first receiving assembly may include a side plate 308, a luer 309, seals 310, 316, 319a, and 319b, and gas channels 322a and 322b, as shown in FIGS. 13-15. Luer 309 may receive one of gas lines 901 and 902. The luer may be configured to prevent decompression should a gas line becomes inadvertently disconnected from the luer. Seals 310, 316, 319a, and 319b (such as o-ring seals) may maintain gas flow within gas channels 322a and 322b, as shown in FIG. 15. Arrows within the gas channels illustrated in FIG. 15 show direction of gas flow through the first receiving assembly.

Lock assemblies 630 of instrument assembly support apparatus 70 may additionally, or alternatively, include a third lock assembly 660, as shown in FIGS. 30-34. That lock assembly may be mounted to or supported in any suitable location. For example, third lock assembly 660 may be mounted to frame 401 of sliding assembly 400. The third lock assembly may include any suitable structure configured to lock second portion 409 of the sliding assembly and/or prevent a user from sliding instrument assembly 600 along longitudinal axis C. For example, third lock assembly 660 may include first and second pressure pads 403a and 403b, and at least one bias element 405.

First pressure pad 403a may include a first channel portion 403a1, while second pressure pad 403b may include a second channel portion 403b1. Second portion 409 may be disposed within those channel portions between the first and second pressure pads. In some embodiments, the channel portions may face each other to form a channel 410 through which second portion 409 may extend between the first and second pressure pads. Bias element 405 (such as a spring) may urge the first and second pressure pads apart. Alternatively, or additionally, first portion 406 may be disposed within the channel portions between the first and second pressure pads and/or extend between those pads.

Although third lock assembly 660 is shown to include particular structure, the third lock assembly may alternatively, or additionally, include one or more components that are the same as or similar to the components of any of the other lock assemblies described in this disclosure. Additionally, or alternatively, the third lock assembly may include one or more components of the locking assemblies disclosed in U.S. Pat. Nos. 5,957,423 and 7,670,281, the complete disclosures of which are hereby incorporated by reference for all purposes.

Figure 30:
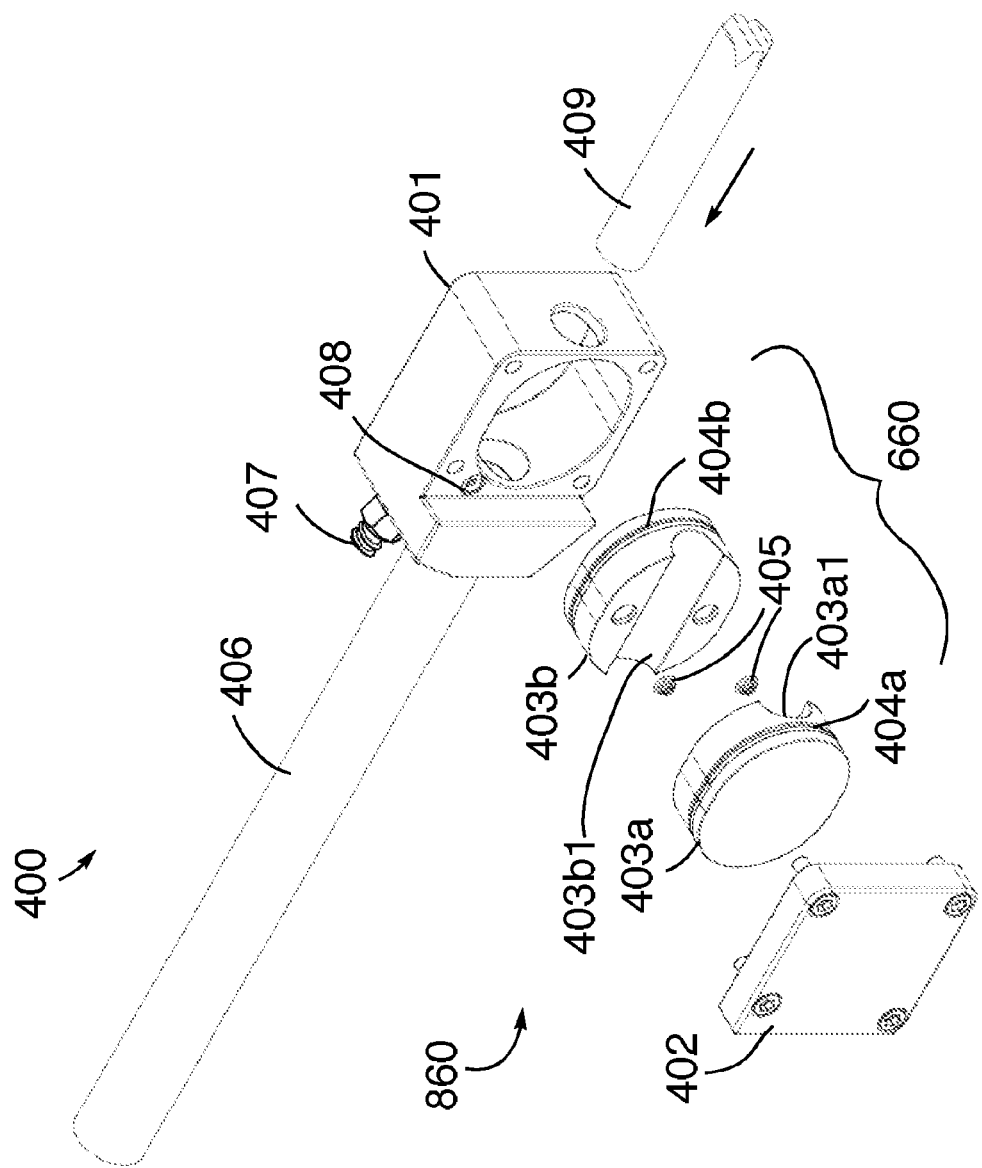
FIG. 30 is an exploded view of a sliding assembly of the instrument assembly support apparatus of FIG. 2.
Figure 31:
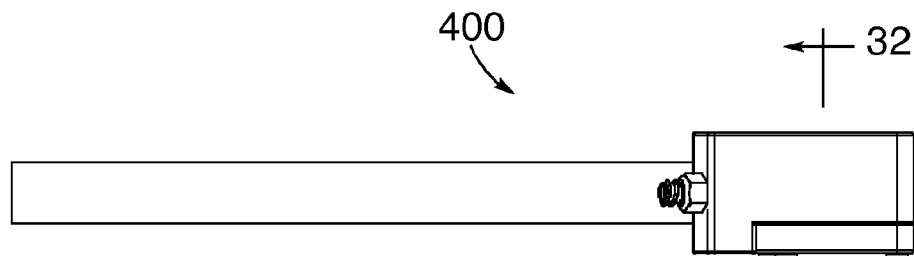
FIG. 31 is a top partial view of the sliding assembly of FIG. 30, showing the sliding assembly with a first portion and a housing but without a second portion.
Figure 32:
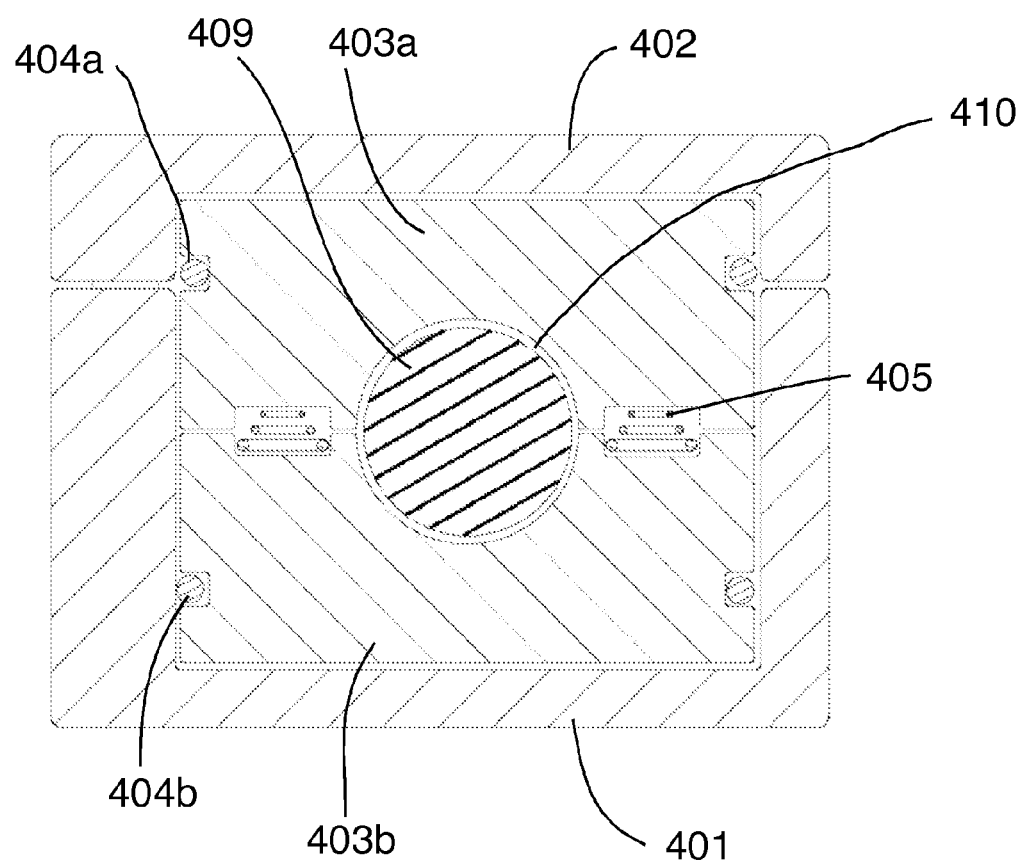
FIG. 32 is a cross-sectional view of the sliding assembly of FIG. 30 taken along lines 32-32 in FIG. 31.
Figure 33:
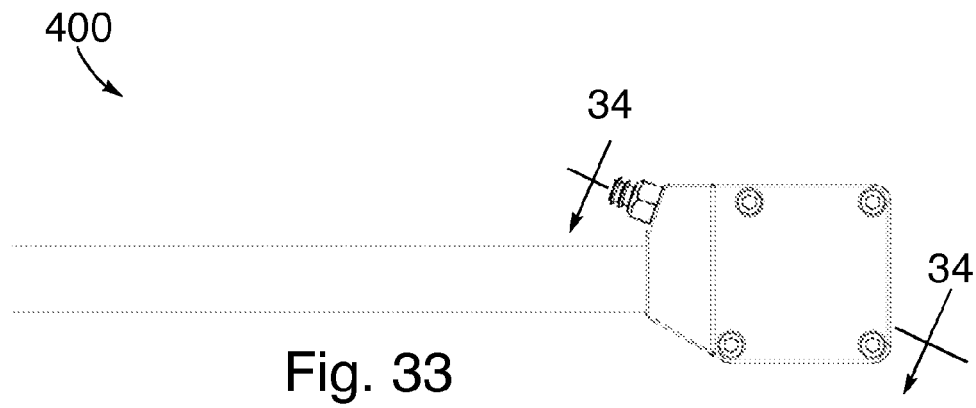
FIG. 33 is a top partial view of the sliding assembly of FIG. 30, showing the sliding assembly with a first portion and a housing but without a second portion.

Biasing mechanism 690 may be configured to interact with the third lock assembly. For example, biasing mechanism 690 may be configured to selectively bias the first and second pressure pads toward the second portion of the sliding assembly. Alternatively, or additionally, the biasing mechanism may be configured to selectively bias the first and second pressure pads toward the first portion of the sliding assembly. The width of the channel formed by the channel portions of the first and second pressure pads may be reduced when those pads move toward each other. When third lock assembly 660 includes bias element 405, the biasing mechanism may be configured to selectively bias the first and second pressure pads toward the second portion against urging from bias element 405. For example, biasing mechanism 690 may include a second receiving assembly 860, as shown in FIG. 30.

Figure 34:
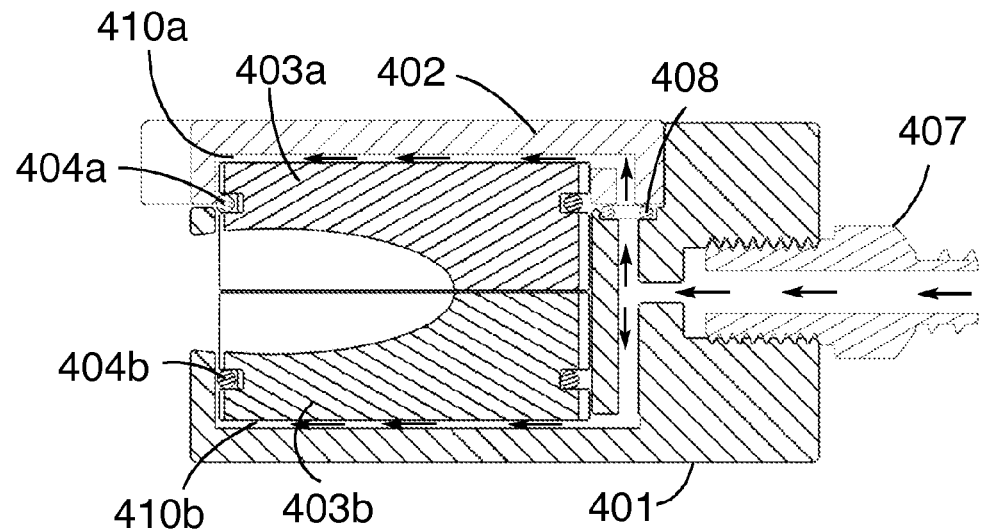
FIG. 34 is a cross-sectional view of the sliding assembly of FIG. 33 taken along lines 34-34 in FIG. 33.

The second receiving assembly may include any suitable structure configured to receive pressurized gas and urge the first and/or second pressure pads toward the second portion against urging from bias element 405. For example, second receiving assembly 860 may include a cap 402, a luer 407, and seals 404a, 404b, and 408, as shown in FIGS. 30 and 34. Luer 407 may receive one of gas lines 901 and 902. The luer may be configured to prevent decompression should a gas line becomes inadvertently disconnected from the luer. Seals 404a, 404b, and 408 (such as o-ring seals) may maintain gas flow within gas channels 410a and 410b, as shown in FIG. 34. Arrows within the gas channels illustrated in FIG. 34 show direction of gas flow through the first receiving assembly.

Lock assemblies 630 of instrument assembly support apparatus 70 may additionally, or alternatively, include a fourth lock assembly 670, as shown in FIGS. 35-37. That lock assembly may be mounted to or supported in any suitable location. For example, fourth lock assembly 670 may be mounted to frame 501 of support assembly 500. The fourth lock assembly may include any suitable structure configured to lock ball 602 of instrument assembly 600 and/or prevent a user from moving instrument assembly 600 along axes D, E, or F. For example, fourth lock assembly 670 may include a pressure pad 503. Pressure pad 503 may include a curvilinear face 503a that conforms to a portion 602a of ball 602.

Although fourth lock assembly 670 is shown to include particular structure, the third lock assembly may alternatively, or additionally, include one or more components that are the same as or similar to the components of the first, second, and/or third lock assemblies. Additionally, or alternatively, the fourth lock assembly may include one or more components of the locking assemblies disclosed in U.S. Pat. Nos. 5,957,423 and 7,670,281, the complete disclosures of which are hereby incorporated by reference for all purposes.

Biasing mechanism 690 may be configured to interact with the fourth lock assembly. For example, biasing mechanism 690 may be configured to selectively bias curvilinear face 503a and/or pressure pad 503 toward portion 602a and/or ball 602. Biasing mechanism 690 may include a third receiving assembly 870, as shown in FIG. 37.

The third receiving assembly may include any suitable structure configured to receive pressurized gas and urge curvilinear face 503a and/or pressure pad 503 toward portion 602a and/or ball 602. For example, third receiving assembly 870 may include a seal 504 and a luer 506, as shown in FIG. 37. Luer 506 may receive one of gas lines 901 and 902. The luer may be configured to prevent decompression should a gas line becomes inadvertently disconnected from the luer. Additionally, gas lines 901 and/or 902 may include one or more valves (not shown) configured to prevent decompression should the gas line(s) become inadvertently disconnected. Seal 504 (such as an o-ring seal) may maintain gas flow within gas channel 507.

Although instrument assembly support apparatus 70 is shown to include the first, second, third, and fourth lock assemblies, any suitable number of lock assemblies may be used. Additionally, although the first, second, third, and fourth lock assemblies are shown to include different components, those assemblies may have similar and/or the same components. Moreover, although the first, second, third, and fourth lock assemblies are shown to be at least partially contained within the frames of pivot assembly 300, sliding assembly 400, and support assembly 500, one or both lock assemblies may be at least partially external the frames.

Figure 57:
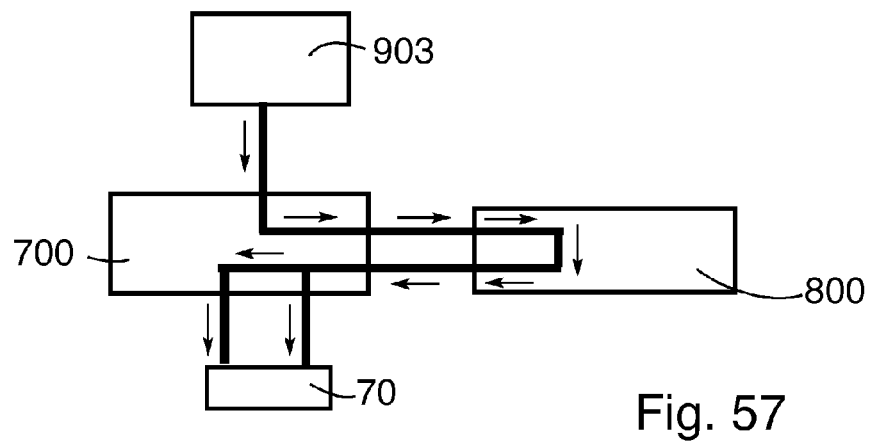
FIG. 57 is a schematic view of the instrument assembly support apparatus of FIG. 2, showing gas flow through the apparatus when a switch of a gas supply assembly is in an "on" position and a foot pedal of a pedal assembly is in an "up" position.
Figure 58:
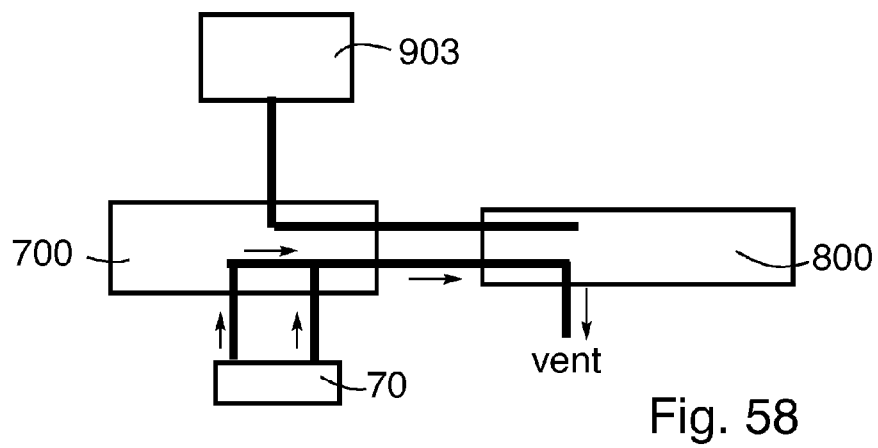
FIG. 58 is a schematic view of the instrument assembly support apparatus of FIG. 2, showing gas flow through the apparatus when the switch is in the on position and the foot pedal of the pedal assembly is in a "down" position.
Figure 59:
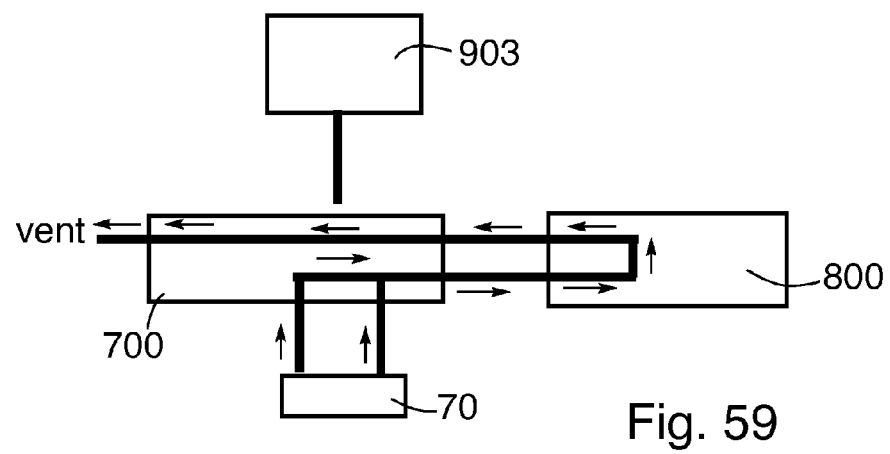
FIG. 59 is a schematic view of the instrument assembly support apparatus of FIG. 2, showing gas flow through the apparatus when the switch is in an "off" position and the foot pedal of the pedal assembly is in the up position.

In operation, a user may lock movement of instrument assembly 600 by having switch 702 in the "on" position and foot pedal 803 in the "up" position. In those positions, gas may flow from pressurized gas supply 903, through gas supply assembly 700 and pedal assembly 800, and to the lock assemblies of the instrument assembly support apparatus, as shown in FIG. 57. When the user desires to move the instrument assembly, the user may press the foot pedal to the "down" position. Movement of that pedal may isolate the instrument assembly support apparatus from the pressurized gas supply at the pedal assembly and allow the pressurized gas in the lock assemblies to vent, as shown in FIG. 58. When the user moves switch 702 in the "off" position and the foot pedal in the "up" position, the instrument assembly support apparatus may be isolated from the pressurized gas supply at the gas supply assembly. Additionally, or alternatively, pressurized gas in the instrument assembly support apparatus (including pressurized gas contained within the gas lines and lock assemblies via the luers and/or gas line valves) may be drained or vented to the atmosphere allowing a user to move the instrument assembly and/or to disassemble the instrument assembly support apparatus, such as between procedures.

Although the instrument assembly support apparatus and features of the instrument assembly support apparatus have been shown and described with reference to the foregoing operational principles and preferred embodiments, those skilled in the art will find apparent that various combinations of features may be used that may be less than all of the features shown, and changes in form and detail may be made without departing from the spirit and scope of the claims. The present disclosure is intended to embrace all such alternatives, modifications, and variances that fall within the scope of the appended claims.

What is claimed is:

1. An instrument assembly support apparatus for supporting an instrument assembly relative to a patient positioned adjacent to an external frame, comprising:
   a base fixedly mountable onto the external frame;
   a pivot assembly mounted relative to the base and including a housing, a first pivot structure pivotably mounted to the housing and fixedly mounted to the base, and a second pivot structure pivotably mounted to the housing, the housing being configured to pivot relative to the first pivot structure and the external frame about a first pivot axis, and the second pivot structure being configured to pivot relative to the housing about a second pivot axis, wherein the housing includes two opposed and spaced side portions and a base portion connecting the two side portions to define a gap between the two side portions, the second pivot structure being disposed within the gap with at least one surface of the second pivot structure extending through the gap over a range of pivot positions about the second pivot axis;
   an arm assembly extending along a longitudinal axis and having a first portion mounted to the at least one surface of the second pivot structure for pivoting relative to the housing, and a second portion extending distally of the first portion;
   a support assembly mounted to the second portion and configured to support the instrument assembly on the arm assembly; and
   a first lock assembly mounted to the housing and configured to be remotely actuated to lock the first pivot structure relative to the housing, the first lock assembly including first and second opposing planar faces intersected by the first pivot axis, a first stop, and a biasing mechanism, wherein the first face is mounted to the first pivot structure, wherein the second face is disposed to move normal to the first face, wherein the first stop is configured to prevent pivoting of the second face about the first pivot axis, and wherein the biasing mechanism is configured to selectively bias the second face toward the first face.

2. The instrument assembly support apparatus of claim 1, further comprising a second lock assembly mounted to the housing and configured to be remotely actuated to lock the second pivot structure relative to the housing, wherein the second lock assembly includes third and fourth opposing planar faces, wherein the second pivot structure includes fifth and sixth opposing planar faces, and wherein the third and fourth faces are disposed to move normal to the fifth and sixth faces.

3. The instrument assembly support apparatus of claim 2, wherein the biasing mechanism is configured to selectively bias the third and fourth faces toward the fifth and sixth faces, respectively.

4. The instrument assembly support apparatus of claim 3, wherein the biasing mechanism includes a control device connected to a pressurized gas supply, wherein the control device is configured to selectively provide pressurized gas to the first lock assembly to urge the second face toward the first face.

5. The instrument assembly support apparatus of claim 4, wherein the control device is configured to selectively provide the pressurized gas to the second lock assembly to urge the third and fourth faces toward the fifth and sixth faces, respectively.

6. The instrument assembly support apparatus of claim 1, wherein the first pivot structure includes one of at least a first pin and a first groove, and the housing includes the other of the at least a first pin and a first groove, the at least a first pin being received in the first groove and the first groove being configured to limit pivoting of the housing relative to the first pivot structure within a first predetermined number of degrees.

7. The instrument assembly support apparatus of claim 6, wherein the second pivot structure includes one of at least a second pin and a second groove, and the housing includes the other of the at least a second pin and a second groove, the at least a second pin being received in the second groove and the second groove being configured to limit pivoting of the second pivot structure relative to the housing within a second predetermined number of degrees.

8. The instrument assembly support apparatus of claim 1, wherein the base includes a grip assembly and a connector assembly, the grip assembly including a grip and an elongate support member, the grip being configured to selectively grip the external frame and the elongate support member extending away from the grip, the connector assembly being attached to the elongate support member and configured to selectively receive the first pivot structure.

9. The instrument assembly support apparatus of claim 8, where the external frame includes a rail that extends along a rail axis, wherein the first pivot structure is selectively received in the connector assembly such that the first pivot structure extends along an axis parallel to the rail axis.

* * * * *